(12) United States Patent
Conner et al.

(10) Patent No.: US 9,581,625 B2
(45) Date of Patent: *Feb. 28, 2017

(54) ANALYSIS OF STIMULUS BY RFID

(71) Applicant: U.S. Photonics, Inc., Springfield, MO (US)

(72) Inventors: Jacob Conner, Strafford, MO (US); Ryan Giedd, Springfield, MO (US)

(73) Assignee: U.S. Photonics, Inc., Springfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/697,309

(22) Filed: Apr. 27, 2015

(65) Prior Publication Data

US 2015/0233986 A1     Aug. 20, 2015

Related U.S. Application Data

(63) Continuation of application No. 13/685,374, filed on Nov. 26, 2012, now abandoned, and a continuation of application No. 13/685,393, filed on Nov. 26, 2012, now abandoned, and a continuation of application No. 13/685,423, filed on Nov. 26, 2012, now abandoned, and a continuation of application No. 13/685,436, filed on Nov. 26, 2012, now abandoned, and a continuation of application No. 13/685,455, filed on Nov. 26, 2012, now abandoned, and a continuation of application No. 13/685,470, filed on Nov. 26, 2012, now Pat. No. 9,016,586.

(51) Int. Cl.
*G06K 19/06* (2006.01)
*G01R 23/02* (2006.01)
*G06K 19/077* (2006.01)
*G06K 19/07* (2006.01)

(52) U.S. Cl.
CPC ........... *G01R 23/02* (2013.01); *G06K 19/077* (2013.01); *G06K 19/0717* (2013.01); *G06K 19/07749* (2013.01); *G06K 19/0723* (2013.01)

(58) Field of Classification Search
CPC ............. G06K 19/0717; G06K 19/077; G06K 19/0723; G06K 19/07749; G01R 23/02
See application file for complete search history.

(56) References Cited

U.S. PATENT DOCUMENTS

| | | | | |
|---|---|---|---|---|
| 6,617,963 | B1* | 9/2003 | Watters | G01D 5/48 340/10.41 |
| 7,659,823 | B1* | 2/2010 | Killian | G06K 19/0717 340/572.1 |
| 7,673,513 | B2* | 3/2010 | Gortler | G01P 15/06 73/514.01 |
| 7,714,593 | B2* | 5/2010 | Varpula | G06K 19/0717 324/654 |

(Continued)

*Primary Examiner* — Claude J Brown
(74) *Attorney, Agent, or Firm* — Da Vinci's Notebook, LLC

(57) ABSTRACT

The present invention is directed to an RFID device. The RFID device includes a brace affixed to an inductor or capacitor. The brace is constructed from a material structurally responsive to a predetermined stimulus, such that stimulus-responsive structural alterations to the brace structurally alters the inductor, capacitor, or other RFID subcomponent of the RFID circuit capable of generating a current alteration, which in turn alters the signal frequency of the RFID.

20 Claims, 19 Drawing Sheets

(56) References Cited

U.S. PATENT DOCUMENTS

| | | | | |
|---|---|---|---|---|
| 8,717,146 B2* | 5/2014 | Potyrailo | ............ | G06K 7/10009 |
| | | | | 340/10.1 |
| 8,925,371 B2* | 1/2015 | Humbert | .............. | G01N 27/223 |
| | | | | 73/29.01 |
| 8,947,236 B2* | 2/2015 | Forster | ................. | G06K 19/077 |
| | | | | 340/10.4 |
| 9,097,745 B2* | 8/2015 | Steinwandel | ........ | G01N 17/043 |
| 2005/0007239 A1 | 1/2005 | Woodard et al. | | |
| 2010/0225482 A1* | 9/2010 | Kasai | ................. | G06K 19/0717 |
| | | | | 340/572.1 |
| 2012/0092027 A1* | 4/2012 | Forster | ................... | G05D 22/02 |
| | | | | 324/658 |

\* cited by examiner

* The lines, which are reproduced in black-and-white, descend in according to the values of the rightward key such that the top line represents 5.00mm and the bottom line represents 20.0mm.

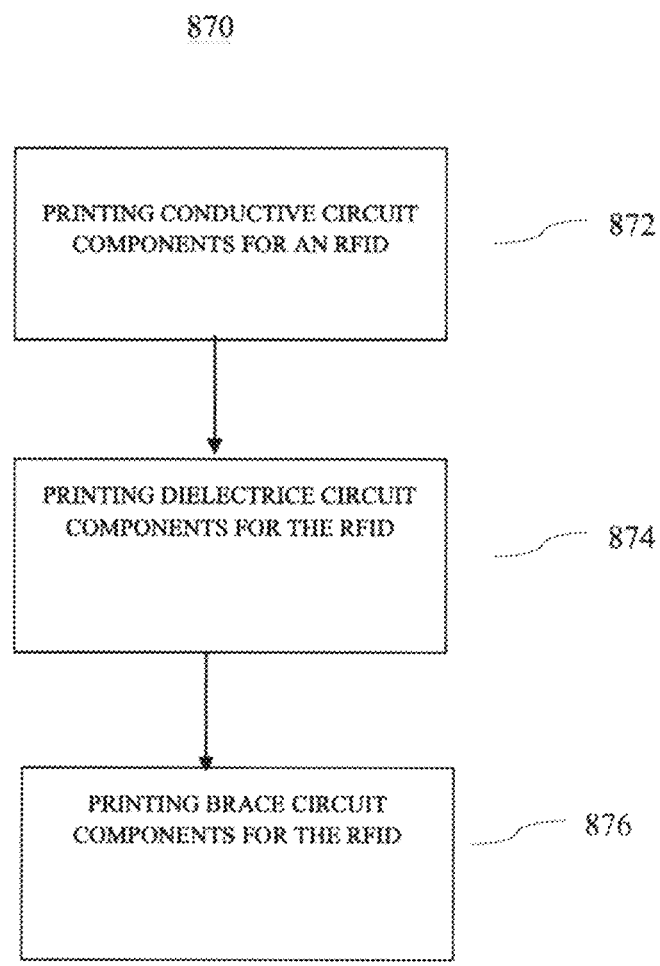

ANALYSIS OF STIMULUS BY RFID

RELATED APPLICATIONS

This application is a continuation of, and claims priority under 35 U.S.C. §120 from, U.S. patent application Ser. Nos. 13/685,374; 13/685,393; 13/685,423; 13/685,436; 13/685,455; 13/685,470 all title ANALYSIS OF STIMULUS BY RFID and all filed Nov. 26, 2012 and the disclosures of which are hereby incorporated by reference.

FIELD OF THE INVENTION

The present invention relates to the field of signal transmission analysis and more specifically to the field of radio frequency identification assisted system analysis.

BACKGROUND

Radio frequency identification (RFID) technology is commonly used for storing and transmitting information associated with a specific object. RFID technology utilizes a tag transponder, which is placed on the object, and a reader, also referred to herein as an interrogator or transmitter/receiver, to energize, read and identify the tag. RFID technologies are broadly categorized as using either "active" tags or "passive" tags. Active tags have a local power source (such as a battery) so that the active tag sends a signal to be read by the interrogator. Active tags have a longer signal range. "Passive" tags, in contrast, have no internal power source. Instead, passive tags derive both processing and transmitting power from the transmitter, and re-transmits information back to the reader. Existing technologies for passive tags typically have a much shorter signal range (typically less than 200 feet).

Both categories of tags have electronic circuits that are typically in the form of an integrated circuit or transistor array based on silicon or metal oxide "chip" technology. The circuit stores and communicates identification and other data to the reader. In addition to the chip, the tag includes an antenna that is directly connected to the chip. Active tags incorporate an antenna that communicates with the reader from the tag's own power source. For passive tags, the antenna also acts as a transducer to convert radio frequency (RF) energy originating from the reader to electrical power. The chip then becomes energized and performs the processing and communication function with the reader.

"Nonactive" component RFID tags or just nonactive tags (sometimes referred to as "chipless" tags) are inherently passive and operate without using any active electronic components or semiconducting materials including integrated circuit(s) or any active discrete electronic components, such as the transistors or diodes. This feature allows nonactive tags to be printed directly onto a substrate at much lower costs than traditional RFID tags using widely available bar code printing technologies such as spray or screen printing.

As a practical matter, RFID in general, and specifically nonactive tag technologies use lower radio frequencies which have much better materials penetration characteristics, will work under more hostile environmental conditions, and do not require geometrical alignment (i.e. do not need a direct line-of-sight between tag and reader) compared to bar code reading technologies. Therefore, nonactive tags may be read through paint, water, dirt, dust, human bodies, concrete, or through the tagged item itself. Similar to traditional RFID tags, nonactive tags may be used in managing inventory, automatic identification of cars on toll roads, security systems, electronic access cards, keyless entry and in reporting environmental conditions.

The principle element of RFID tags that are typically prepared via stamping/etching techniques is the RF antenna, where a foil master is carved away to create the final structure with specified frequency response. The RFID antenna may also be printed directly on the substrate using a conductive metal or polymer ink. The ink is printed on a substrate, followed by high temperature sintering used to anneal the particles and to create a conductive pathway or line on the substrate. Alternatively, metal fibers may be incorporated directly into the substrate. Although particulate metal materials may be used, the superior characteristics of nanoparticle metal materials suspended in conductive organic inks results in a better product. Metallic nanoparticles are particles having a diameter in the submicron size range. Nanoparticle metals have unique properties, which differ from those of bulk and atomic species. Metallic nanoparticles are characterized by enhanced reactivity of the surface atoms, high electric conductivity, and unique optical properties. For example, nanoparticles have a lower melting point than bulk metal, and a lower sintering temperature than that of bulk metal. The unique properties of metal nanoparticles result from their distinct electronic structure and from their extremely large surface area and high percentage of surface atoms.

Metallic nanoparticles are either crystalline or amorphous materials. They can be composed of pure metal, such as silver, gold, copper, etc., or a mixture of metals, such as alloys, or core of one or more metals such as copper covered by a shell of one or more other metals such as gold or silver. The nozzles in an inkjet printing head can be less than 1 um in diameter. In order to jet a stream of particles through a nozzle, the particles' size should be less than approximately one-tenth of the nozzle diameter. This means that in order to inkjet a particle, its diameter must be less than about 100 nm.

Nickel or iron particles have been used for conductive inks for a very limited extent because of its relatively low conductivity (approximately four times less than that of copper). However in nonactive tags such magnetic materials may be required for enhanced inductor performance. Gold and silver can provide good electrical conductivity without magnetic effects, but are relatively expensive. Moreover, gold and silver require high temperatures for annealing, which can pose a challenge for printing on paper and plastic substrates. Copper provides good conductivity at a low price (about one percent of that of silver). Unfortunately, copper is easily oxidized and the oxide is non-conductive.

Copper-based nanoparticle inks are unstable and require an inert/reducing atmosphere during preparation and annealing in order to prevent spontaneous oxidation to non-conductive CuO or $Cu_2O$. Copper polymer thick film (PFT) inks have been available for many years and can be used for special purposes, for example, where solderability is required. Another interesting strategy is to combine the advantages of both silver and copper. Silver plated copper particles are commercially available, and are used in some commercially available inks. Silver plating provides the advantages of silver for inter-particle contacts, while using the cheaper conductive metal (copper) for the bulk of the particle material. Thus, the preferred reliable means of preparing copper antennae is via electroplating on an existing metal surface.

No current technology exists for an inexpensive bio-organic or organic/metal particle composite based RFID nonactive tag structure that permits identification and environmental parameters to be associated with an item.

A printed antenna with passive and non-active discrete components or an entirely printed circuit including the antenna and the passive components are two paths towards the inexpensive production of high quality nonactive RFID tags. However, because RFID tags do have internal digital electronic circuitry, the capacity of nonactive RFID tags to store large amounts of data is limited. Nevertheless, nonactive RFID tags are an ideal vehicle for use in measurement systems involving multiple items with requiring tags that are very inexpensive, simple to produce, environmentally friendly and biodegradable. Thus there is a need for a tag structure, such as nonactive RFID tags, that provides item identification and environmental information.

SUMMARY

The present invention is directed to an RFID device, a process for determining the effects of stimulus on an item, and a measurement system. The RFID device includes an inductor, a conductive antenna complex, and a brace. The inductor is a passive two-terminal electrical component that stores energy in its magnetic field. The conductive antenna complex includes one or more antennae that connect to the inductor. The portions of the antenna complex that connect to the inductor are elastic to compensate for the motioning of the inductor that forms a part of the present invention. The antennae complex is arranged to accept a predetermined base frequency.

The brace may be affixed to the inductor, preferably along multiple points. A preferred version of the brace is a brace carriage that houses the entirety of the inductor. The brace is constructed of a material structurally responsive to a predetermined stimulus. The stimulus may include any effect that influences the effectiveness of an item that is desired to be monitoring for stimulus effects. In response to the stimulus the brace volume may be altered and the expansion of the brace distorts the inductor. The distorted inductor alters the frequency of a response signal as generated by the antenna complex. The measurement system of the present invention includes the RFID device placed proximate to an item.

The brace may be affixed to the capacitor, preferably to alter the potential difference between capacitor portions. A preferred version of the brace is a brace carriage interleaved between the layers of the capacitor. The brace is constructed of a material structurally responsive to a predetermined stimulus. The stimulus may include any effect that influences the effectiveness of an item that is desired to be monitoring for stimulus effects. In response to the stimulus the brace volume may be altered and the expansion of the brace distorts the capacitor. The distorted capacitor alters the frequency of a response signal as generated by the antenna complex. Furthermore, any component of the circuit in which an alteration of current through the circuit affects the signal generated by the RFID may be acted upon by the carriage brace of the present invention.

The difference between the predetermined base frequency and the frequency of the response may be measured to determine the effects of the stimulus upon the item. The process for determining the effects of stimulus on an item includes associating the RFID with the item. For example, the RFID device may be placed on an item that is desired to be monitored for stimulus effects. A space with one or more RFID devices of the present invention is radiated with an interrogation signal series based on the predetermined frequency. The interrogation signal series includes one or more signals in a range correlated to the predetermined base frequency. An interrogator accepts a response signal from the RFID device. The predetermined base frequency is then compared to a response signal frequency to measure the effects of the stimulus. The deviation in the response signal frequency to the predetermined base signal frequency is related to the expansion of the brace and also the effects of the stimulus on the item. The resulting response signal may be utilized to inform a variable of a mathematical calculation involving a particular entity of stored items of the present invention.

Furthermore, the present invention includes a method for constructing a capacitor. The capacitor is constructed using a set of stencils for electrode layers and dialectric layers of the present invention. It is preferred that the electrode layers include a stencil with a void for both the electrode portion and the terminal leads therefor. The electrode layers are sprayed about a distinct dielectric layer or a designated portion of the substrate.

Furthermore, the present invention includes a system and process for clean measurement of an item in a combustion scenario. An RFID device constructed entirely of organic components is associated with the item and is substantially combusted by the item or a separate energizer.

These aspects of the invention are not meant to be exclusive. Furthermore, some features may apply to certain versions of the invention, but not others. Other features, aspects, and advantages of the present invention will be readily apparent to those of ordinary skill in the art when read in conjunction with the following description, and accompanying drawings.

BRIEF DESCRIPTION OF THE DRAWINGS

FIG. 20 is a view of a process of manufacturing an RFID of the present invention.

DETAILED DESCRIPTION

Figure 1:
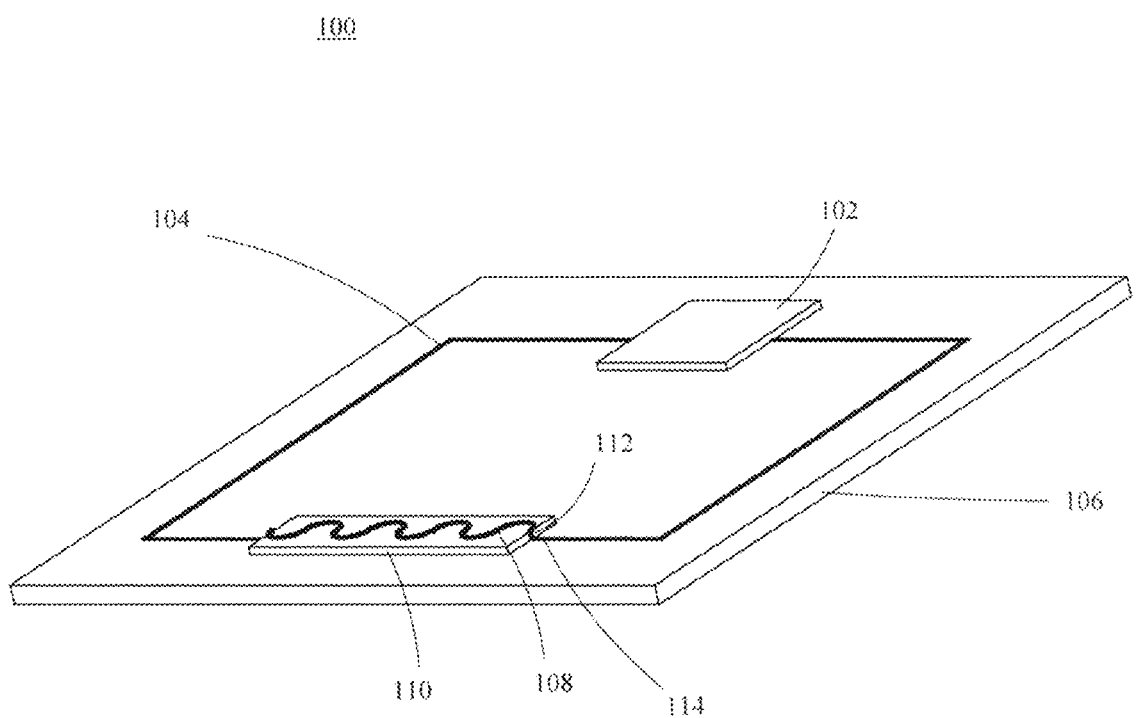
FIG. 1 is a view of the device of the present invention.

Referring first to FIG. 1, a basic embodiment of the radio frequency identification ("RFID") device 100 is shown. The RFID device 100 includes an inductor 108, and antenna complex 104, a brace 110, and a capacitor 102 in one possible configuration of an LC circuit. The RFID device 100 is manufactured to include one or more circuit components, preferably the capacitor or the inductor, attached to the brace 110. The brace upon exposure to an external stimulus alters its dimensions and thereby contorts the circuit component(s) connected thereto. The contorted circuit component alters the signal transmitted by the circuit; this altered signal differs from the signal that the circuit would transmit in the absence of exposure to the stimulus, i.e., the original signal or predetermined base signal (or frequency). The altered signal conveys information regarding the stimulus conditions to a recipient of the transmission.

The inductor 108 of the present invention may include one or more inductors as commonly used in the art. The radio frequency inductor 108 is a passive two-terminal component whose electronic impedance is selected to conform to predetermined signal characteristics, e.g. frequency. The inductor may be constructed of a geometrically flat conductor whose length is determined by the wavelength of a preferred signal characteristic. Due to the time-varying magnetic field surrounding the inductor, a voltage is induced, according to Faraday's law of electromagnetic induction, which by Lenz's law opposes the change in current that created it. Inductors are one of the basic components used in electronics where the phase and timing between current and voltage maximums can be adjusted depending on excitation frequency.

A major factor for high performance radio frequency integrated inductor is the quality factor (Q). The objective of high-Q inductor designs is to provide accurate inductance at the lowest possible resistance while keeping parasitic capacitance to a minimum. In this manner highly selective and sharp bandpass oscillation frequencies can be achieved. The quality of an inductor, QL, is determined by the ratio of the magnitude of the inductive reactance to the resistance:

$$Q_L = \frac{\omega L}{R}$$

Here, omega is the angular frequency of the electrical signal, L the value of the inductance for an inductor, and the R the pure resistance of a conducting line. As the frequency increases, for a given L, the Q increases. The use of high quality factor components in a resonant circuit for the present invention assists in obtaining more measurable tag responses in the frequency spectrum.

It is preferred from the printed component and antenna geometrical perspective that the nonactive RFID circuit resonates at the lower frequency band of 30 KHz-100 MHz for enhanced penetration through high dielectric constant materials, for example at frequencies less than 100 KHz the signal can penetrate 30 meters of seawater. The figures and calculations are based on a system with a center frequency of 30 MHz.

Figure 4:
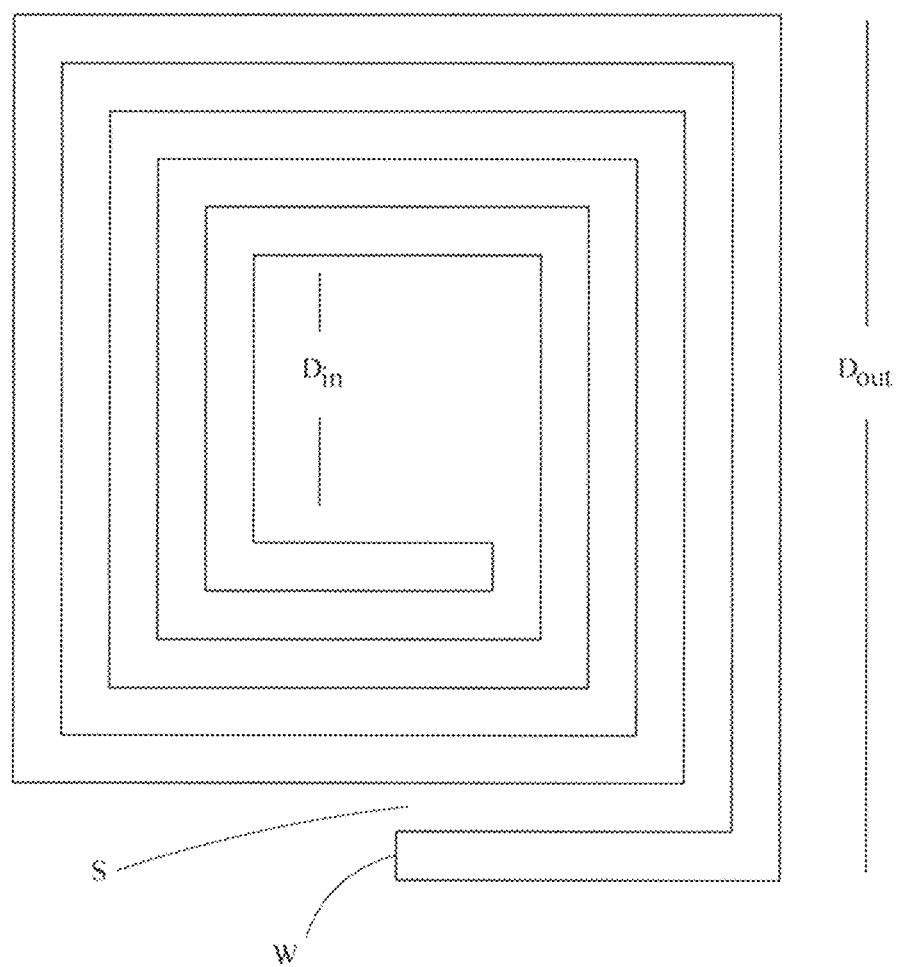
FIG. 4 is a view of the preferred inductor of the present invention.

The response in terms of an EMF generated through around a conducting antenna loop is generally given by Maxwell's equations and is proportional to the strength of the rate of change in the magnetic flux produced by the "transmitter" loop and the number of turns in the antenna complex. The preferred number of antenna turns in the antennae complex is ten or less. Turning now to FIG. 4, the characteristics of the preferred coil design of the inductor is determined by Distance of the interior, $D_{in}$, Distance of the entire inductor, $D_{out}$, Width of the conductor, W, and Space between the wound conductors, S. The preferred Distance of the inductor interior in preferably fixed at 2.00 mm. The preferred width of the trace is equal to the space between the traces, and equal to the width of the coil divided by twice the number of turns. Exemplary inductor characteristics are shown in Table 1.0.

TABLE 1.0

| W, S (um) | Dout (mm) |
| --- | --- |
| 75.00 | 5.00 |
| 106.25 | 6.25 |
| 137.50 | 7.50 |
| 168.75 | 8.75 |
| 200.00 | 10.00 |
| 262.50 | 12.50 |
| 325.00 | 15.00 |
| 387.50 | 17.50 |
| 450.00 | 20.00 |

With a distance of the inductor interior of 2.0 mm and a resonant frequency of 30.0 MHz, the inductance is shown by Table 2.0.

TABLE 2.0

| Inductance (microH) | Dout (mm) |
| --- | --- |
| 0.468 | 5.00 |
| 0.500 | 6.25 |
| 0.539 | 7.50 |
| 0.582 | 8.75 |
| 0.628 | 10.00 |
| 0.722 | 12.50 |
| 0.820 | 15.00 |
| 0.920 | 17.50 |
| 1.020 | 20.00 |

Figure 7:
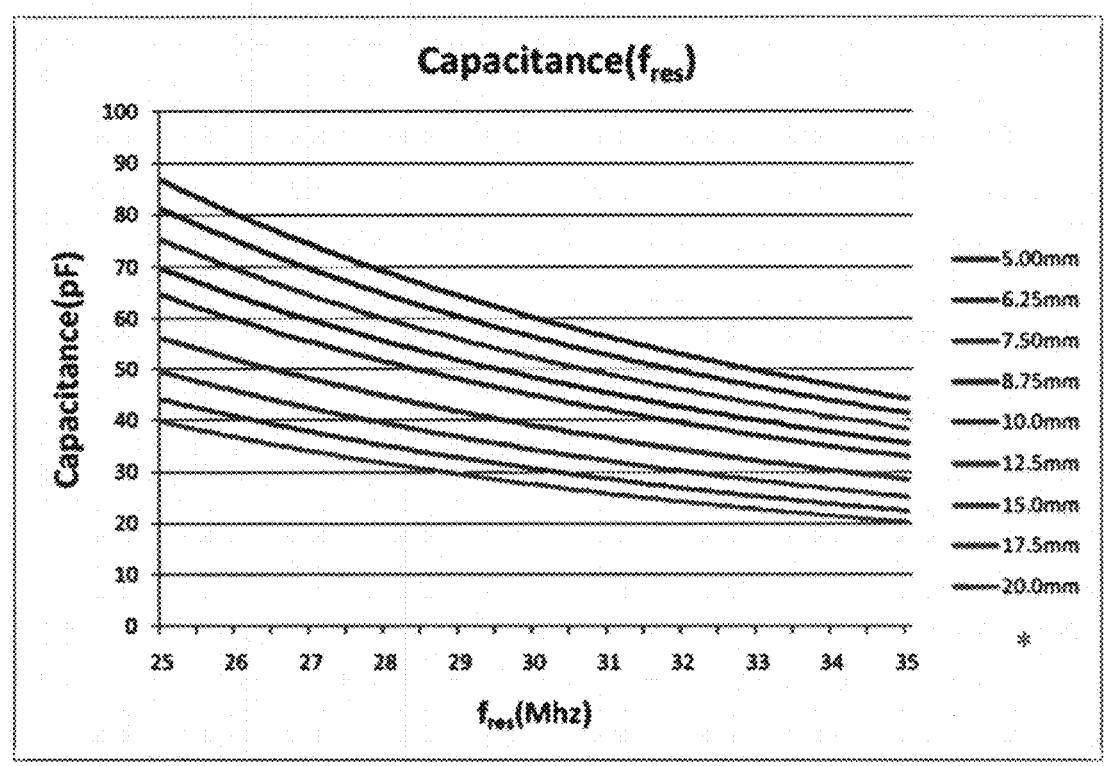
FIG. 7 is a graph of the resonance frequency vs. capacitance for the RFID circuit of the present invention.

With these values for the inductor and the center frequency, the required values for the capacitor in the RFID circuit may be readily calculated. See, e.g. FIG. 7. The graph of FIG. 7 not only depicts values for the capacitor in the circuit for a given frequency; they also demonstrate the variation in frequency with capacitance change. A typical phase-locked loop circuit operating in the frequency band specified above is generally sensitive to frequency changes of only a few hertz, thus a small change in capacitance, as a result of environmental stimulus, e.g. temperature or humidity change, will change the resonant frequency according to the graph of FIG. 7 in such a way to make a readable signal measurable to ascertain the environmental stimulus.

Returning to FIG. 1, a preferred means of creating the inductor 108, antenna complex 104, and capacitor 102 includes inkjet deposit. New inkjets can print very precise patterns of electrically conducting polymers, carbon nanotubes, and organic/metallic nanoparticle composites. Although conventional inkjets are limited to resolutions of about 25 micrometers, recent developments in inject technology, e.g. electrohydrodynamic inkjets, can print lines of a material 700 nanometers wide or individual dots just 250 nanometers in diameter. In addition to decreasing the size of the droplets, the handling processes that permit the minimal size of the droplets also improve the spatial accuracy. The inductor may include any inductor known in the art and may include flat ferromagnetic cores for frequencies in the lower part of the frequency band.

The inductor 108 is affixed to a brace 110. The brace 110 of the present invention is an aggregation of material to which the inductor is attached that dimensionally alters based on a stimulus. The stimulus as meant in the present disclosure includes any effect that influences the effectiveness of an item that is desired to be monitored for stimulus effects. The stimulus should be both natural and external. By external it is meant that the stimulus originates from beyond the physical form of the RFID device and is a phenomenon based on the state of the system (e.g., moisture) in which the RFID device is placed rather than an intra-device phenomenon (e.g., current). The brace is selectively deformable, which means that the structure of the brace is deformable to limited, and predetermined stimulus. Examples of external stimulus include radiation (e.g., UV, neutrons, gamma, beta, alpha, X-ray), harmful chemicals and nerve agents (e.g., VX, Sarin, soman, etc.), decomposition products (e.g, ethylene gas produced by rotting fruits, etc.), corrosive gases (e.g, halogens, ammonia, amines, etc.), biological agents (e.g., anthrax, lysteria, *E-coli*, botulinum, yeast or their metabolites); air or oxygen; hydrocarbons; halocarbons (e.g., Freon), illicit drug residues (e.g., s cocaine, methamphetamine, LSD, marijuana, opiates, etc.), explosive compounds (e.g., nitro group explosives or peroxide based explosives); hormones (e.g., estrogen, testosterone), and exposure to ketones, blood sugars or urine compounds. In response to the stimulus the brace dimensions are altered and the expansion of the brace 110 in turn distorts the geometry of the inductor 108. The dimensionally distorted inductor 108 alters its inductance and thus frequency of a response signal as generated by the antenna complex deviates from that of the base frequency at which the RFID device was created.

Figure 2A:
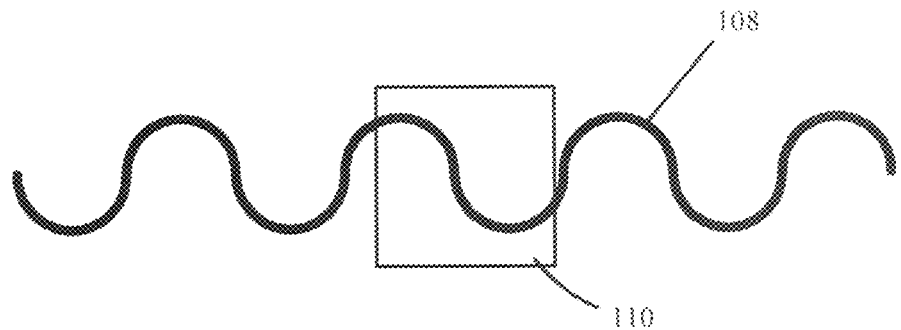
FIGS. 2A-C are views of the brace/inductor complex of the present invention.
Figure 2B:
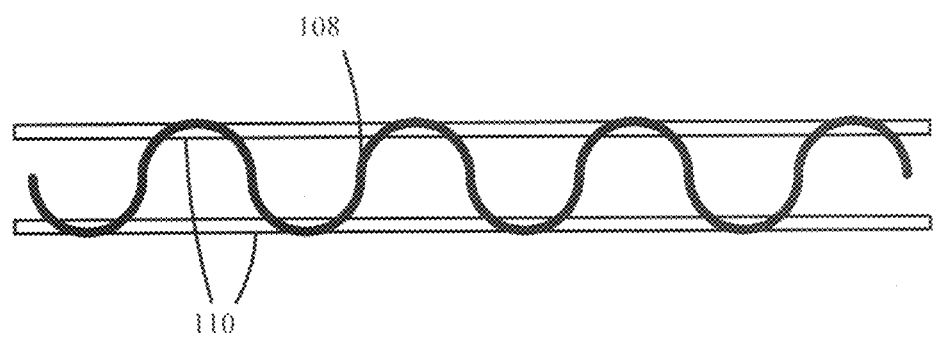
Figure 2C:
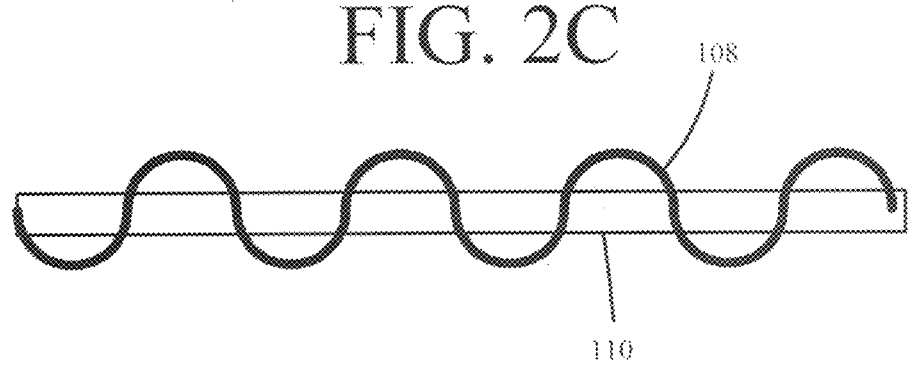
Figure 3A:
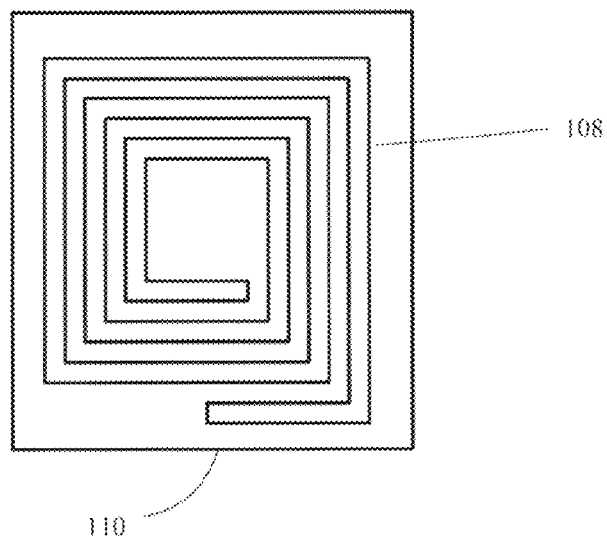
FIGS. 3A-C are views of the brace/inductor complex of the present invention.
Figure 3B:
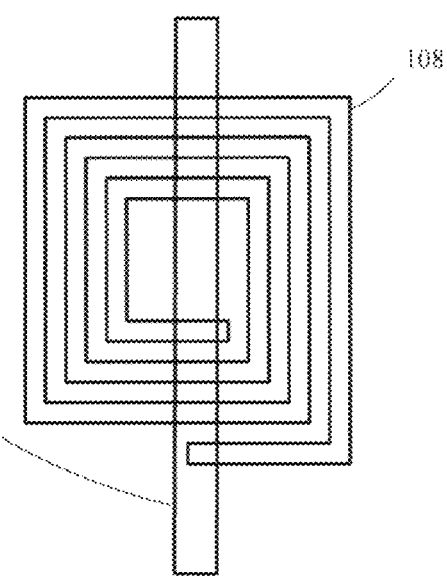
Figure 3C:
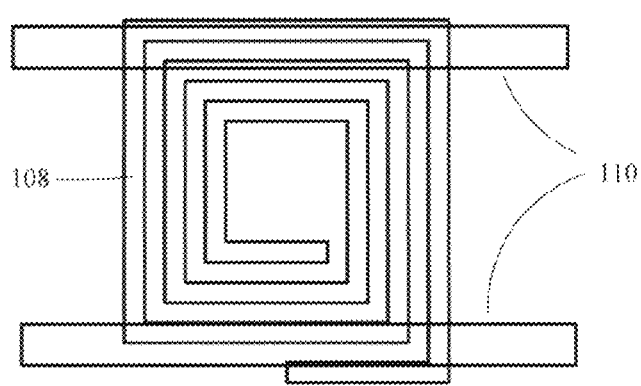

FIGS. 2A-2C and 3A-3C depict exemplary braces 108 of the present invention utilized with both arbitrary inductor configurations, FIGS. 2A-2C, and the preferred inductor configuration, FIGS. 3A-3C. As shown in FIG. 2A the inductor 108 may only be partially affixed to the brace 110. Selective portions of inductor geometrical distortion may be measured for reliable information. As shown in FIGS. 2B-2C and FIGS. 3B-3C, it is preferred that the brace 110 contact a substantial portion of the inductor such as from one extremity of the inductor to the other. Such braces affect with substantial effect the $D_{out}$ measurements of the RFID device. The end-to-end brace 108 may comprise one or more portions arranged as desired in order to acquire useful measurements on the item. The carriage brace depicted in FIG. 1 and FIG. 3A are the preferred embodiments of the brace. The carriage brace 110 contains the entirety of the inductor 108 such that the brace exerts the greatest influence on the inductor 108. It is preferred that in any brace/inductor subsystem that the brace directly contact the substrate 106 with the inductor 108 supported above the substrate 106 by the brace 110.

The brace may be constructed of any material responsive to a stimulus. Preferred stimulus-sensitive materials include those with a linear coefficient of expansion. The brace may be a temperature-sensitive material so that it expands during periods of relative heat and contracts during periods of relative cool. Such braces may be termed bi-directional braces as the brace dimensions are capable of both contraction and expansion in a repeatable process. The bi-directional braces may be particularly useful when contemporaneous stimulus effects matter more than extended stimulus effects. For example, without the aid of any equipment other than that found in a tank circuit, e.g., no chip or external sensor device, the tank circuit becomes a circuit sensor that can read present environmental conditions. The brace can be synthesized from a host of materials including "memory" materials that undergo geometrical shape transformations as a function of local environment. In order of growing complexity these include thermally expanding polymers, moisture sensitive organic materials, meta-stable materials (that contract or expand with time), chemical sensitive materials that react (expand or contract) with chemicals present in the environment, and bio-sensitive materials that when exposed to specific or generic biological change their shape. Meta-stable, temperature-sensitive and moisture-sensitive materials are inherently useful in constructing a unidirectional brace for any generic nonactive tag.

The above technologies assume reversibility; a unidirectional brace is a brace that once it has expanded or retracted cannot engage in the opposition reaction. For examples, the swelling of hydrogel, absent use of additional construction devices, cannot be reversed such the brace contracts at a later time—irrespective of respective diminishment in humidity. Unidirectional braces are ideal for permanently altering the dimensions of the inductor such that the RFID device measures the prolonged or cumulative effects of stimulus. The materials inherently conducive to unidirectional and bi-directional braces need not constrict the use of brace to either a unidirectional and bi-directional nature. For example, the use of temperature sensitive material, e.g. polystyrene, may be constructed to include spaced protrusion that meet with spaced protrusion on the substrate such that the brace operates like a ratchet and a material inherently conducive to contraction cannot contract.

As the inductor 108 connects to a capacitor 102, and any other materials desired to be included in an RFID circuit, the inductor and conductive trace that constitutes the antenna 104 are required to be flexible, or at least have flexible portions. The spatial alterations of the inductor 108, caused by the spatial alterations of the brace, apply a net strain to the conductive trace material of the antenna 104. In extreme circumstances, and with standard materials as used in the art, the inter-inductor material, inter-antenna material, or connection points between the antenna and inductor may produce strain to the point of fissure and failure of the tag. It is preferred in the present invention, that the inductor, particularly the termini 112 portions thereof, and at least the antenna complex 114 proximate to the brace be constructed of a material that is both conductive and flexible. Carbon nanotubes or conductive polymers are candidates that may fulfill this role admirably.

The alterations in the dimensions of the inductor in turn alter the resonant frequencies at which the RFID circuit interacts with the interrogation signals and transmits response signals. The deviations of the response signals from the nonactive RFID device, when exposed to a wide bandpass interrogation signal, from a predetermined RFID tag frequency spectrum provides information. The specific information describes the stimulus to which the RFID device, and the item to which it was attached, was exposed.

The capacitor 102 of the present invention may include any capacitor known in the art. It is preferred that one or more capacitors are used that provide crisp resonant peaks. Ceramic composite, polycarbonate, polystyrene, and PMMA capacitors may be utilized, however, tag substrate or air gap or capacitors with a minimum dielectric loss in the interrogation signal frequency range are preferred as they are shown to provide clear resonant peaks. The static DC and AC impedance measurements of typical widely used and available radio frequency capacitors can easily provide sufficient Q between 1.0 pF and 10,000 pF, respectively.

For some applications where the tags need to be completely organic, a preferred construction material of the capacitor plates includes electroactive and conductive polymers. Examples conductive polymers that may be candidates for the present invention include Polyaniline (PANI) (p-type) and Poly (BEDOT-BBT)(n-type & p-type). PANI is available from Crosslink Inc. as a brand PAC 1003.

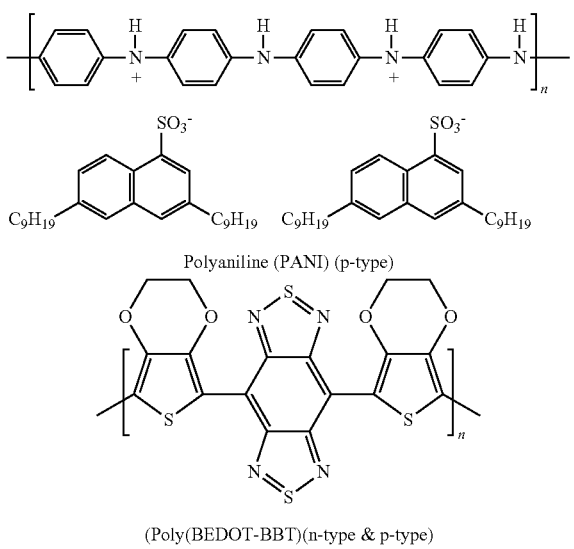

Polyaniline (PANI) (p-type)

(Poly(BEDOT-BBT)(n-type & p-type)

The PANI may be spray coated or spin-coated upon the RFID substrate 106. It is preferred the PANI be spin-coated in the micron range with a preferred thickness of 10.0 microns and a range from 1.5 to 250 microns. The PANI may be spray coated with atactic polypropylene as a binder forming a composite material. Atactic polypropylene may be dissolved in xylenes and toluene at low concentrations to have appropriate viscosity for specific spin or spray coating processes.

Development and printing of conductive traces for the antenna 114, inductor 108, and interconnects may be constructed by screen-printing carbon nanotube suspensions onto an appropriate substrate material such as polyethylene terephthalate (PET) (≤30 Ω/sq), polystyrene, or paper. Conductive materials based on carbon nanotubes ("CNTs") have been successfully screen printed onto PET and silicon for baseline testing of the sheet resistance by Brewer Science Inc. Several different types of tube morphologies were used, including differences in tube length and diameter, and single-walled versus multi-walled. When CNT concentrations were increased to 1 wt % or higher, baseline planer resistances were about 10 Ω/sq on silicon and about 30 Ω/sq on PET. These differences can be attributed to the variable interfacial wetting conditions between the CNT suspension and the substrate, and to differences in post process annealing temperatures between silicon and the plastic substrates.

The above sheet resistances of interconnects are very good for these materials, however, when scaling to larger geometries required for the nonactive tags the resistance per square increases rapidly as a result of CNT morphological variation in larger volumes of material. Therefore, formulations of CNT layers must be made significantly thicker to achieve lower resistances and thus acceptable Q values for the "all organic" nonactive tags. The next step for these screen-printed materials is to focus on the most conductive tubes and to optimize the formulation and deposition parameters so that the resistance of the components and component interconnects improves over the longer lengths required in this frequency band.

Figure 19:
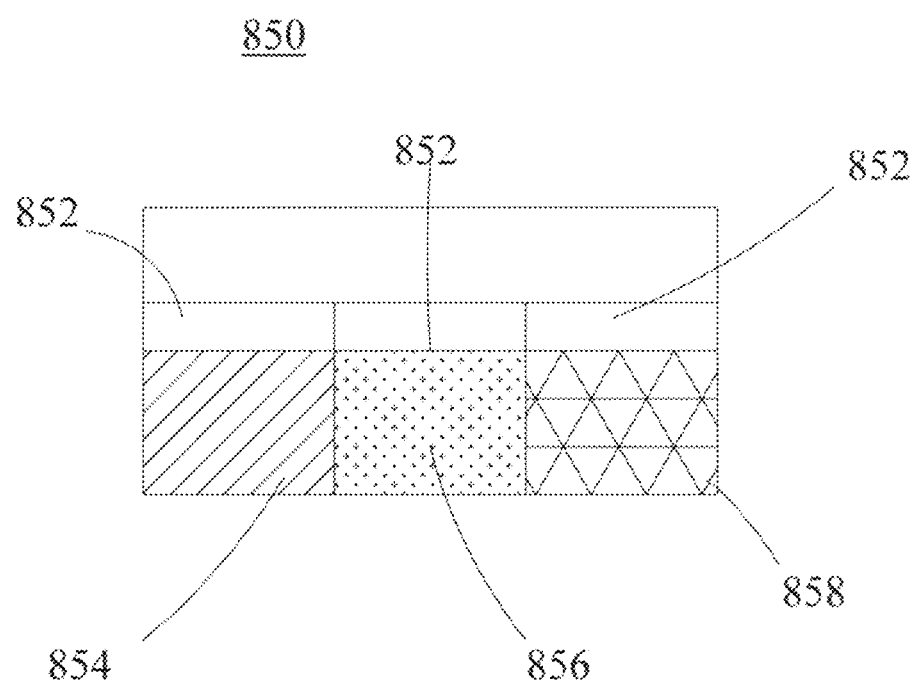
FIG. 19 is a view of the print cartridge of the present invention.

An aerosol jet printer may be used to print conductive CNT inks A 50 Ω, 100×200 micron CNT pad structure may achieved using an aerosol jet printer tested for suitable substrate adhesion. Brewer Science Inc. has shown that a concentrated pure aqueous CNT conductive ink can be printed on Kapton-FPC with an OPTOMEC aerosol jet printer. The CNT concentrations between 1.25 g/L-2.5 g/L were printed successfully using this research grade equipment. Furthermore, the brace of present invention may be printed using a jet printer. In such a jet-printed embodiment the printer may utilize a cartridge including three wells. As shown in FIGS. 19 and 20, the cartridge 850 includes a series of conductor wells 852 that includes conductive material 854, which may utilized in a component printing process 870 to print 872 the circuit and other conducting portions of the circuit, dielectric material 856, which may by utilized to print 874 separating components, and if the dielectric material is responsive to predetermined stimulus then also the brace. A further well 852 may include the brace material 858 for printing 876 on the RFID. Returning to FIG. 1, the CNT inks were printed between two metallic Ag contacts nominally identified as a source (S) and drain (D), however, strictly ohmic or passive component characterization was to determine the percolation threshold resistance of the materials and to make direct comparisons between various CNT distributions. The CNT conducting region was quite small, between 100 and 200 microns, respectively. Resistances of 53Ω were obtained for one of the CNT distributions. The resistance and geometry result in a CNT resistivity of $4.5\times10^{-5}$ Ω-m or conductivity of $2.22\times10^{4}$ S/m. Larger geometry CNT films were printed to determine more practical film conductivity for nonactive tag interconnects and components. A sheet resistance of 135 Ω/sq was obtained for multiple prints, and a sheet resistance of 1000 Ω/sq.

A preferred material for the brace carriage 110 is a polydimethylsiloxane (PDMS)-based polymer for the temperature-sensing version of the nonactive tag design. This polymer is suitable for screen printing given acceptable printing characteristics such as viscosity and working time. The pad designs are with 21 mm, 13 mm, and 10 mm squares to fully encompass variations in $D_{out}$ and the inductor 108. PMDS coatings on PET and Kapton-FPC substrates have been shown by Brewer Science Inc. to be mechanically stable at the 130 to 650 μm range of thickness under reasonable processing conditions. A simple tape test for adhesion indicated a quality PMDS substrate interface with no significant lifting. When processing was done at room temperature the polymer was not fully cured after 24 hours indicating that elevated temperature annealing is necessary. Processing on a conveyor oven at 166 degrees Celsius produced a fully cured material, but some additional flow during the anneal process was observed specifically in the thicker 650 μm coatings. The PMDS films contracted when cooled to room temperature, as expected, but resulted in sufficient strain to wrinkle or curl the substrate. The strain was relieved in another post process anneal. These results and others in the literature indicate that this material should have a coefficient of thermal expansion coefficient of around 300 ppm/C that should result in a measureable center frequency shift of the nonactive tags with temperature.

The capacitor 102 of the nonactive tags may be spray or ink jet coated on top and bottom electrodes to form parallel plate geometry. A preferred material for these plates is the Crosslink Inc. PAC 1003 electrodes that were spray-coated at three different thicknesses on three substrates. The substrates used were Kapton-FPC (polyimide film from DuPont; 75 µm), Poly(ethylene terephthalate) (PET; 75 µm), and Poly(vinylidene difluoride) (PVDF; 28 µm). Spraycoating was carried out using a SONO-TEK spraycoater (from Brewer Science Inc.). The thickness of the capacitor electrodes was varied by producing 3, 5, and 7 layers (or coats) of the material on the substrate. One coat involves spraying in the vertical direction and then in the horizontal direction. The Crosslink Inc. PAC 1003 (17% solids) solution was diluted to a 29.79% solids solution in xylenes/Butyl Cellusolve (BCS) (100/27.39) with xylenes. Capacitor electrodes may be made by spraycoating over the entire area of a stainless steel hard mask having 1.0 to 1.5 cm square openings. The substrate may be rotated, and a second film spray-coated on the opposite side so that the two electrodes are form a capacitor with an area of about 2.00 $cm^2$ and a dielectric consisting of the substrate.

To improve the conductivity of the electrodes and thus the Q of the capacitor, the plate electrodes may be exposed to thymol vapor and subsequent secondary doping. Thymol vapor cleaning may be performed by adding thymol (~¼") to a stainless steel rectangular container (2"×12"×6") and heating to 150° C. The electrodes are suspended over thymol vapor for about 60 minutes. Post thymol processing consists of a thermal anneal in an oven at 150° C. for 30 minutes and slow cool back to room temperature. Secondary doping is achieved by submerging the electrodes for 60 minutes in a stainless steel container filled with a 60 C 5% p-toluene sulfonic acid (PTSA)/0.5% p-toluene sulfonamide (PTSAm) BCS solution.

Figure 5A:
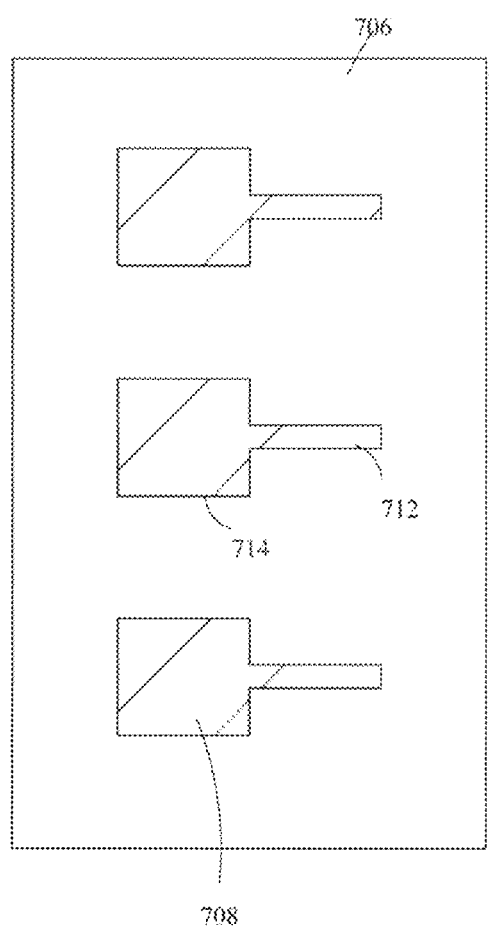
FIGS. 5A-B are views of stencils of the present invention.
Figure 5B:
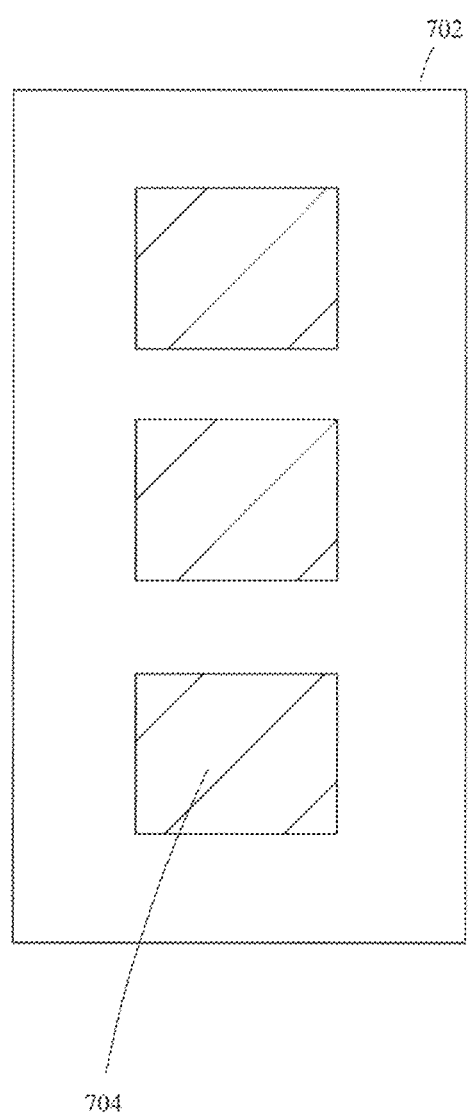
Figure 15:
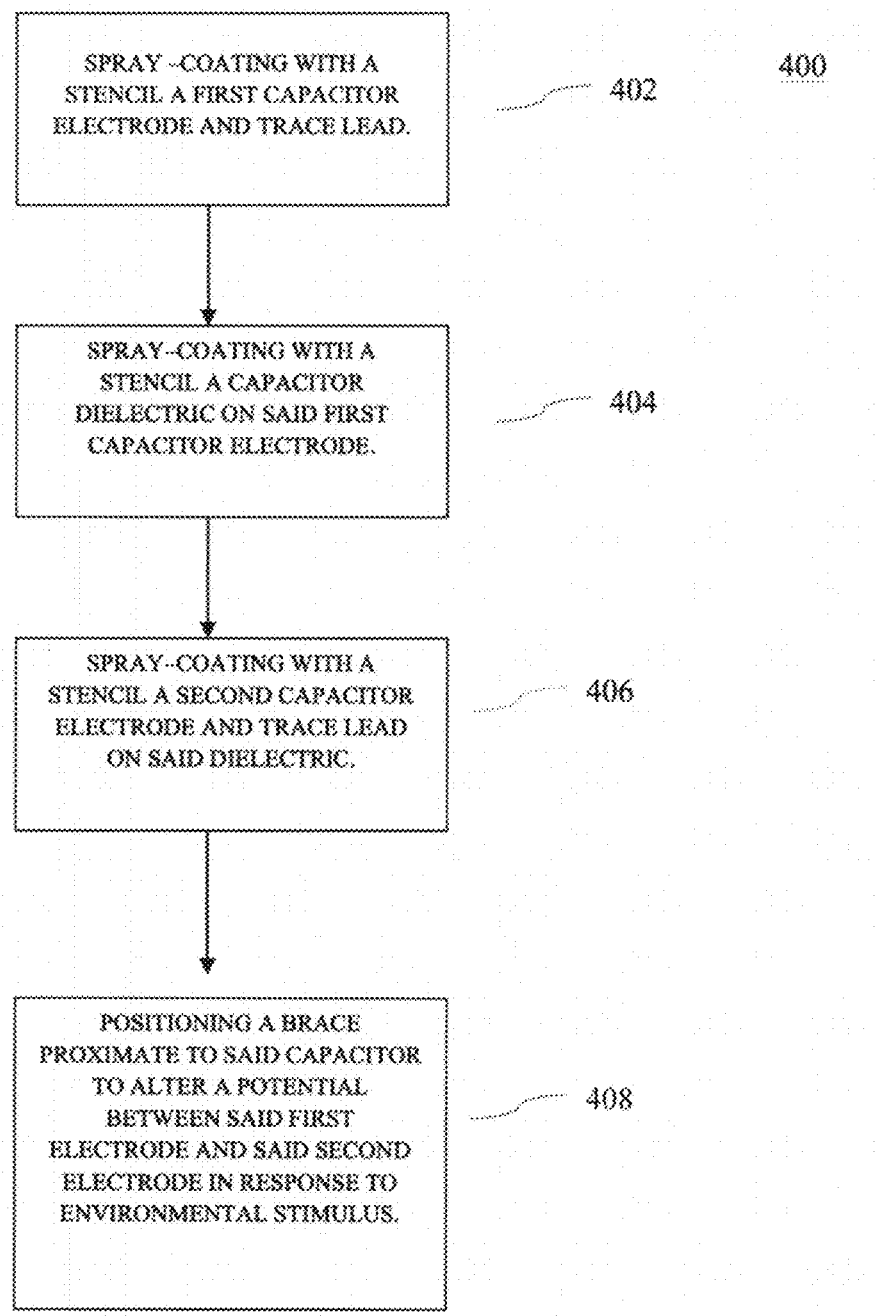
FIG. 15 is an embodiment of a process of constructing a capacitor of the present invention.

Turning to FIGS. 5A-5B and 15 another preferred method for preparing the capacitor 102 component is to spray coat 402, 406 the Corosslink Inc. PAC 1003 electrodes with three thicknesses on a Kapton-FPC substrate using a SONO-TEK spray-coater from Brewer Science Inc. The total capacitor electrode thickness is a functions of spray-coating 1, 2, and 3 layers, where one layer results in one coat. The PAC 1003 (17% solids) solution described above. The capacitor electrodes were spray-coated onto the substrate in a rectangular geometry (100 mm×190 mm), thermally annealed in an oven at 150° C. for 30 minutes, and cut into square sections for subsequent post processing. The electrode sections were treated by room temperature submersion for 0.5, 1, 2, or 4 minutes in 40 mL of a 5% PTSA/0.5% PTSAm BCS solution with stirring rate of 100 rpm. The electrodes were subsequently dried and heat treated in an oven at 130 C for 10, 20, and 30 minutes.

Surface resistance measurements of the post processed capacitor electrodes can be measured by either surface resistivity or a four point measurement system. Capacitance measurements must be taken with care at the higher frequency ranges because of parasitic contributions from short interconnects and the significant dielectric loss factor. In addition substrate morphology must be monitored so that "microholes" do not cause shorting between the capacitor electrodes.

The totally organic spray-coated capacitors with different conductivity enhancement processes performed significantly different in the higher frequency ranges. The above exemplary capacitance requirement for the thermal sensor is 0.025-0.06 nF or 25 to 60 pF at 30 MHz. Capacitance measurements of spray-coated nonactive tags, having a 75 µm PET dielectric and substrate with an effective capacitor area of 1.8 $cm^2$ were determined by quasi static CV measurements. The tags were scanned for three cycles from 0 to 0.8 mV at 25, 50, 75, and 100 mV/s. These low frequency measurements were established as a baseline performance with the cycle from 1600 mV and 100 mV/s. The highest to lowest frequency used for determination of capacitance was 62.5 mHz=(100 mV/s)/(1600 mV) to 15.6 mHz=((25 mV/s)/(1600 mV)). The capacitance was found to be dependent on the electrode or plate PAC 1003 film thickness. This may be the result of charge concentration at the PAC 1003/dielectric interface. Although the capacitance measurements were performed under lower frequencies, the baseline capacitance values fall within the range of the required capacitance for the overall system.

Figure 8:
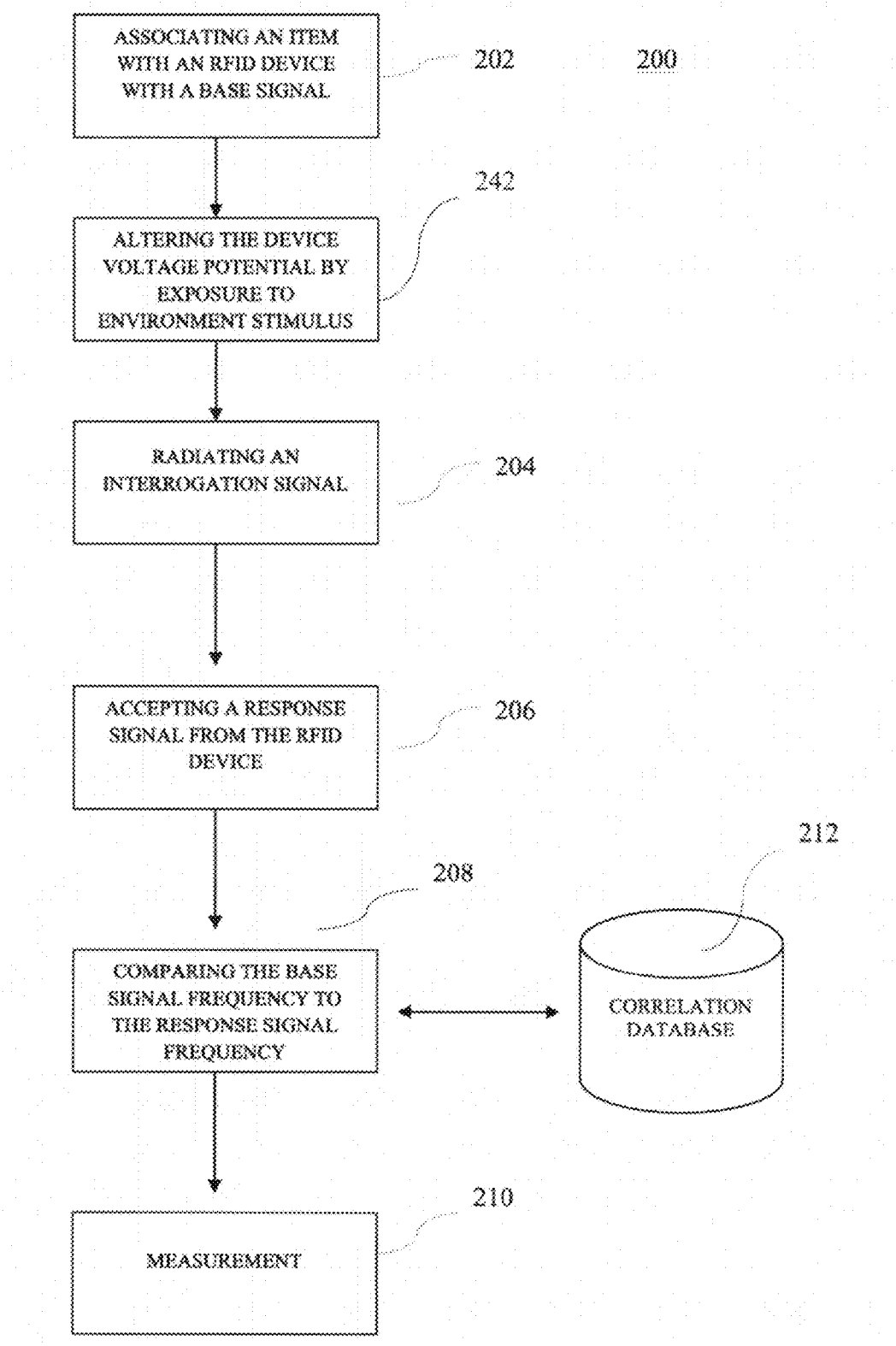
FIG. 8 is the frequency response of the nonactive tags to the RFID interrogator at the low end of the frequency range.

Returning to FIG. 1, the capacitor 102, inductor 108 and antenna network 114 may additionally be prepared using more standard organic/metallic particle systems and established inks. In this implementation a series of inks more consistent with materials accepted for food packaging or agricultural applications may be advantageous provided that the overall nonactive tag structure biodegradable and environmentally friendly. For this case much of the processing and characterization stated above remains the same, however, for these more established inks the screen printing method would be preferred with respect to expense and speed. Of special note would be Fe or Ni containing nanoparticle inks where much larger inductors could be implemented resulting in nonactive tag frequencies in the lower regions of the frequency range listed above. One such low frequency nonactive tag response is shown in FIG. 8. At these frequencies, the penetration depth of the RFID interrogation signal and the nonactive tag response is much higher and for example can penetrate up to 30 m of seawater, a highly electrically conductive high loss material. Such performance is gained at the expense of nonactive tag read time which in these cases should be between 10.0 and 100.0 mSec, nevertheless fast enough for most applications.

Figure 6A:
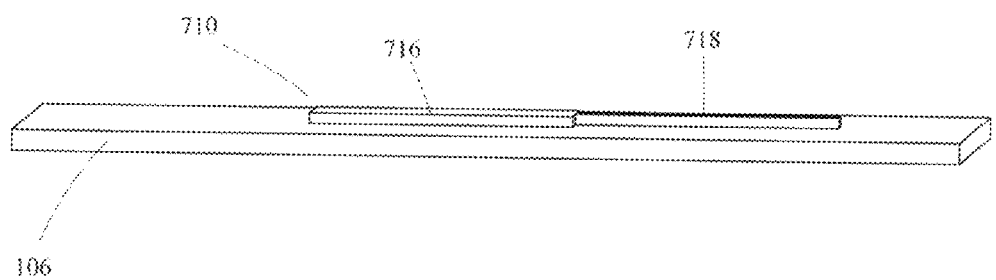
FIGS. 6A-C are views of the construction of the preferred capacitor of the present invention.
Figure 6B:
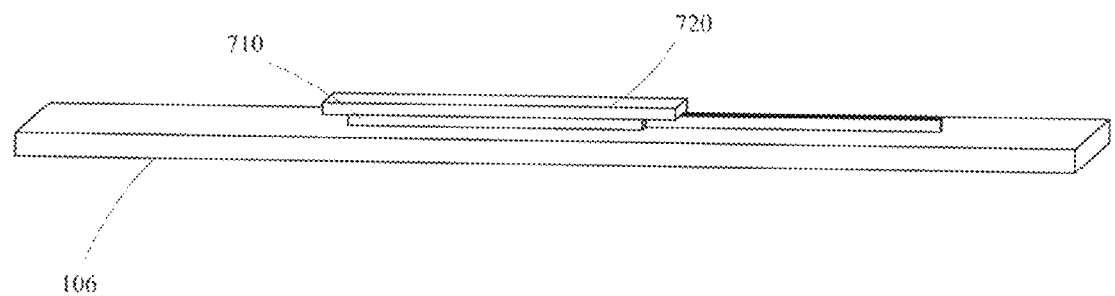
Figure 6C:
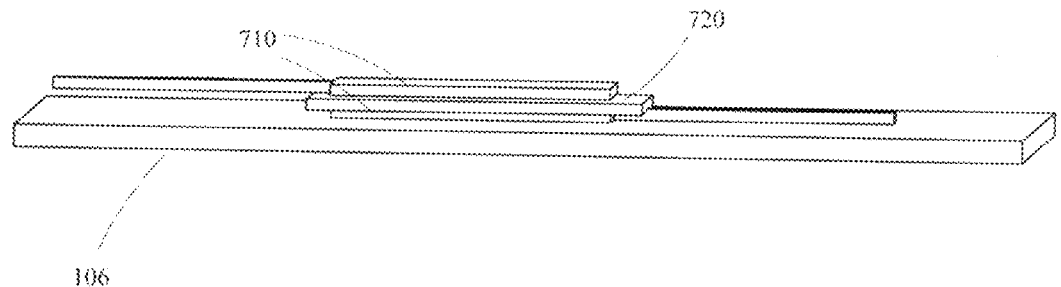

The preferred means of manufacturing capacitors is depicted in FIGS. 5A-B, 6A-C, and 15. Molybdenum hard mask stencils 702, 706 were prepared and used to fabricate fully printed the capacitors as depicted in FIG. 6C. The lowest surface resistance obtained from a 2.5 $cm^2$ film was 7.0 Ω/sq. The electrode stencil 706 included voids 708 with a major void 712 to print 402 the electrode body 716 and a minor void 714 to print the electrode terminus 718. The preferred major void is 1.0 $cm^2$ with a minor void of dimensions 0.2 cm×1.0 cm. As shown in FIG. 6A, the electrode 710 is first printed 402 upon the substrate 106. The dielectric 720 is printed 404 on top of the electrode 710 utilizing the dielectric stencil 702. Upon the dielectric 720 a second electrode 710 is printed 406.

Turning now to FIGS. 11-14, a braced-capacitor embodiment of the RFID device 100 is depicted. Similar to the braced-inductor embodiment, the braced-capacitor embodiment of the RFID device 100 includes a substrate 106, antenna complex 104, inductor 108, capacitor 102, and brace 110. The brace 110 rather than being positioned proximate to the inductor 108 is positioned proximate to the capacitor 102. The brace 110 acts on the capacitor 102 to alter the potential difference between the two charged plates. The preferred means of acting upon the brace 110 is physically distorting to the orientation of the capacitor or components thereof.

Figure 12A:
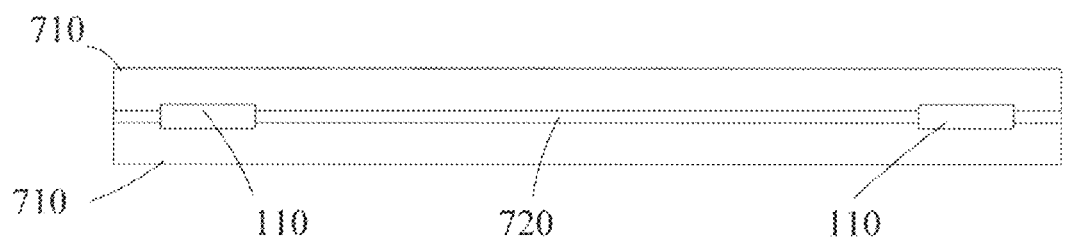
FIGS. 12A-B are views of an embodiment of the capacitor of the present invention.
Figure 12B:
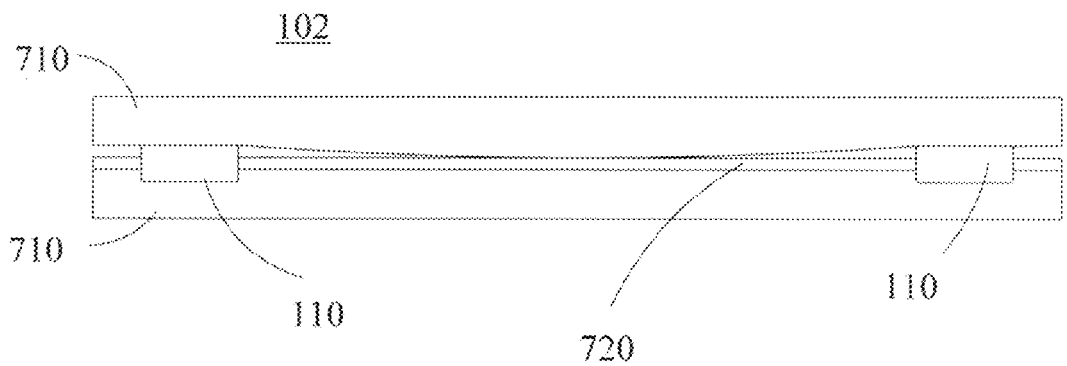
Figure 13A:
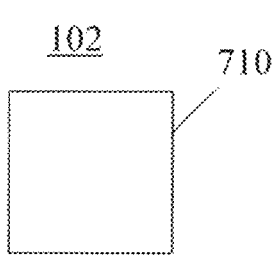
FIGS. 13A-C are construction stage views of embodiments of capacitors of the present invention.
Figure 13B:
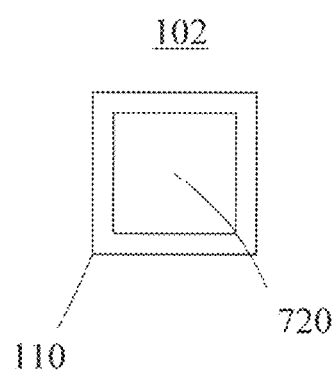
Figure 13C:
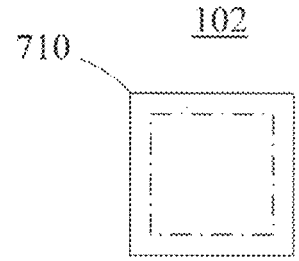
Figure 14:
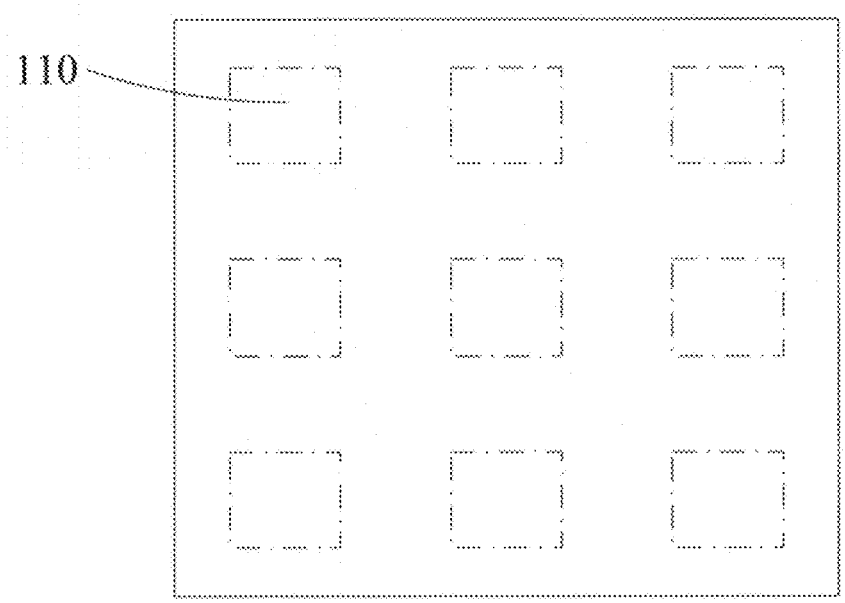
FIG. 14 is an embodiment of an embodiment of a capacitor of the present invention.

The preferred means of physically acting upon the capacitor 102 is depicted in FIGS. 12A-12B. The capacitor 102 may be constructed according to any known means in the art, but includes a brace 110 that is positioned between the electrodes 710. Alterations in the dimensions of the brace 110 in turn alter the orientation of the electrodes 710 and dielectric 720 of the capacitor 102. An initial version of the capacitor is shown in FIG. 12A; upon exposure to an environment that alters the dimensions of the brace 110, the brace 110 pushes portions of the electrodes 710 away one from the other. The alteration of the distance between the electrodes and/or diminished contact with the dielectric alters the potential between the electrodes. The difference between the starting potential and altered potential of the capacitor alters the signal frequency transmitted by the RFID device. This signal frequency alteration results in a response signal frequency that differs from a predetermined base frequency for that particular RFID device, the results of which can be analyzed to measure the environment in which the RFID is, or was, placed. The brace 110 may include the aspects of the general brace of the present invention, merely tailored for application with the capacitor 102. The brace may include may include one or more components as is depicted in FIGS. 11-14, oriented and configured in any manner to alter the potential difference between capacitor electrodes 110 upon exposure of the brace to environmental stimulus.

Figure 16:
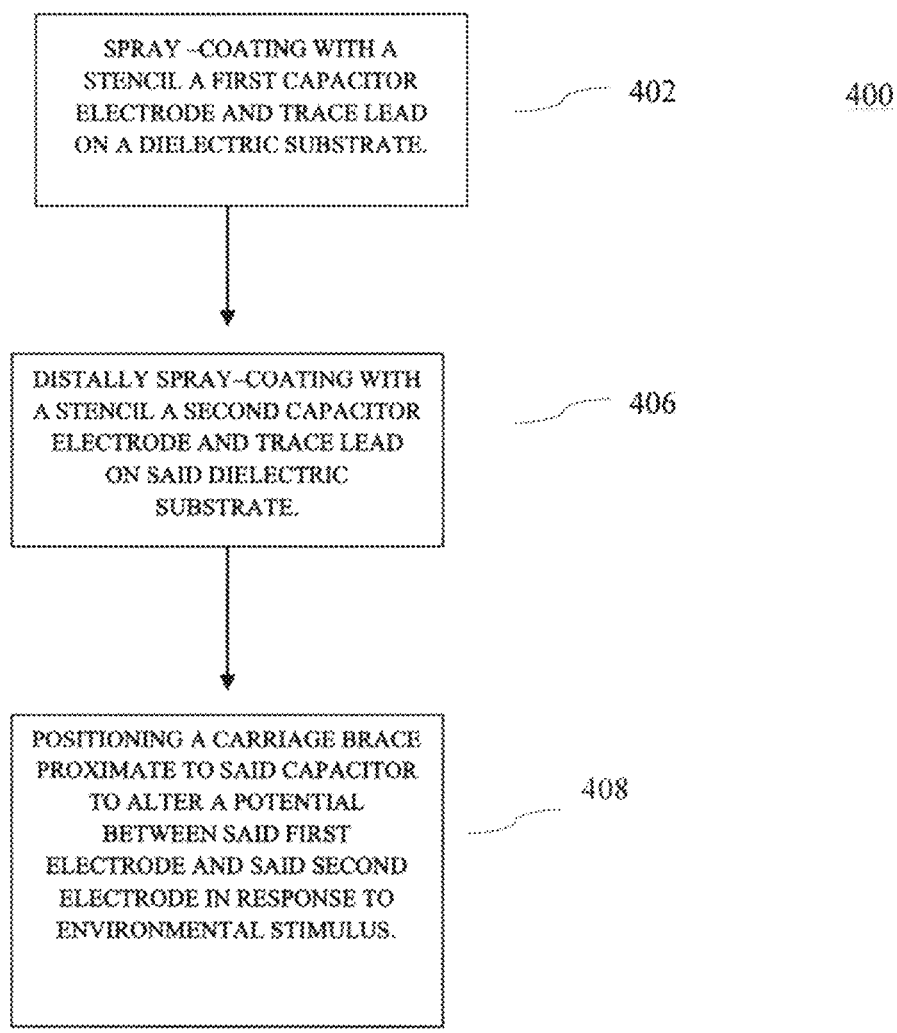
FIG. 16 is an embodiment of a process of constructing a capacitor of the present invention.

Turning to FIGS. 13A-C and 15, the process 400 for manufacturing a capacitor 102 acted upon by a carriage brace 110 is shown. The process 400 includes spray-coating 402 an electrode 710 upon a substrate using stencils such as those depicted in FIGS. 5A-5B. It is preferred the spray-coating step include not only the electrode, but also the leads for the conductive trace stemming from the capacitor. A dielectric 720 is then spray-coated 404 upon the electrode 710 using stencil 702 and dielectric void 704. A second electrode 710 is then spray-coated 406 upon the dielectric 720. A brace 110 is preferably positioned 408 between the electrodes 710 such that physical distortion of the brace 110 results in enlarging the distance between the electrodes or otherwise increasing the potential difference between the electrodes. The brace 110 of FIG. 13B, for example, includes a peripheral brace version inserted between the capacitor layers. As shown in FIG. 16, the present invention may include a capacitor 102 that lacks a distinct dialectric, but rather includes capacitor electrodes 710 sandwiched about the substrate block of the RFID device, which is typically composed of a suitable dielectric material. The electrodes 710 may positioned on opposite surfaces of the substrate directly opposing one another. In other preferred embodiments of the system, the brace may be chosen from a material such that the capacitor dielectric is the brace. In embodiments where the brace is the dialectric, additional deformation structure may not be desired.

Figure 10:
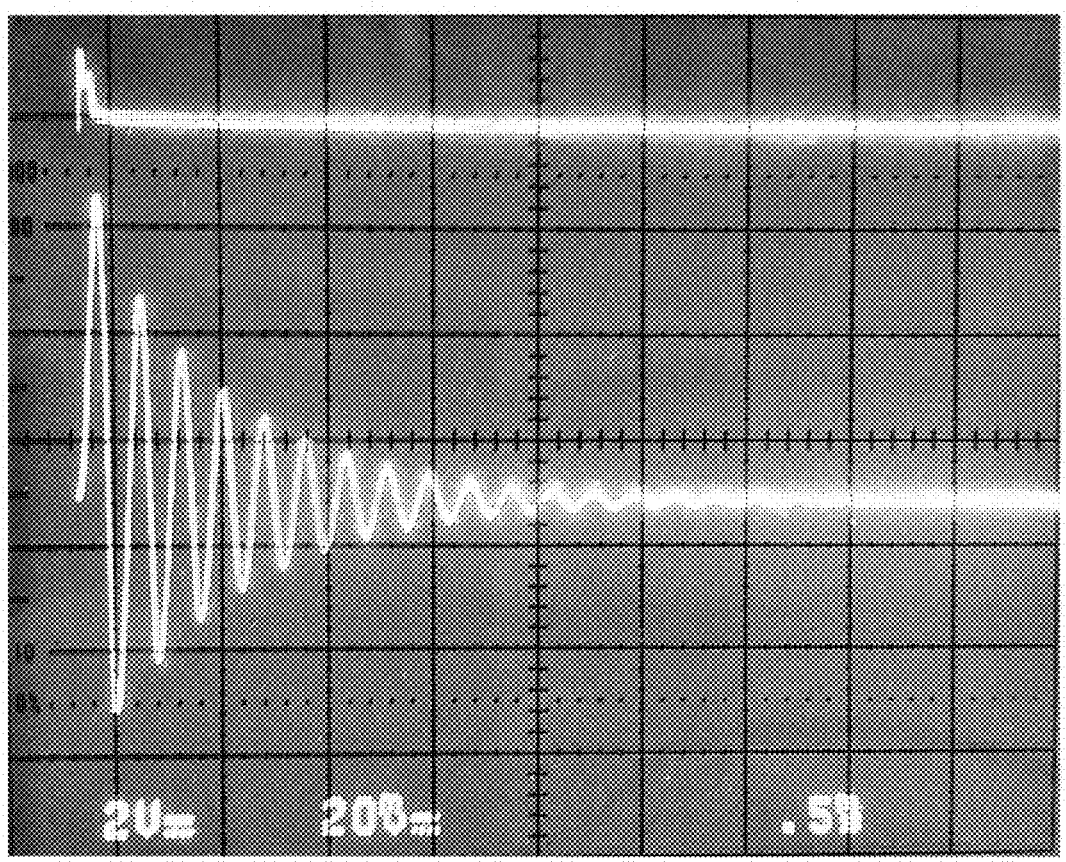
FIG. 10 is a visual depiction of a nonactive tag response after interrogator pulse.
Figure 11:
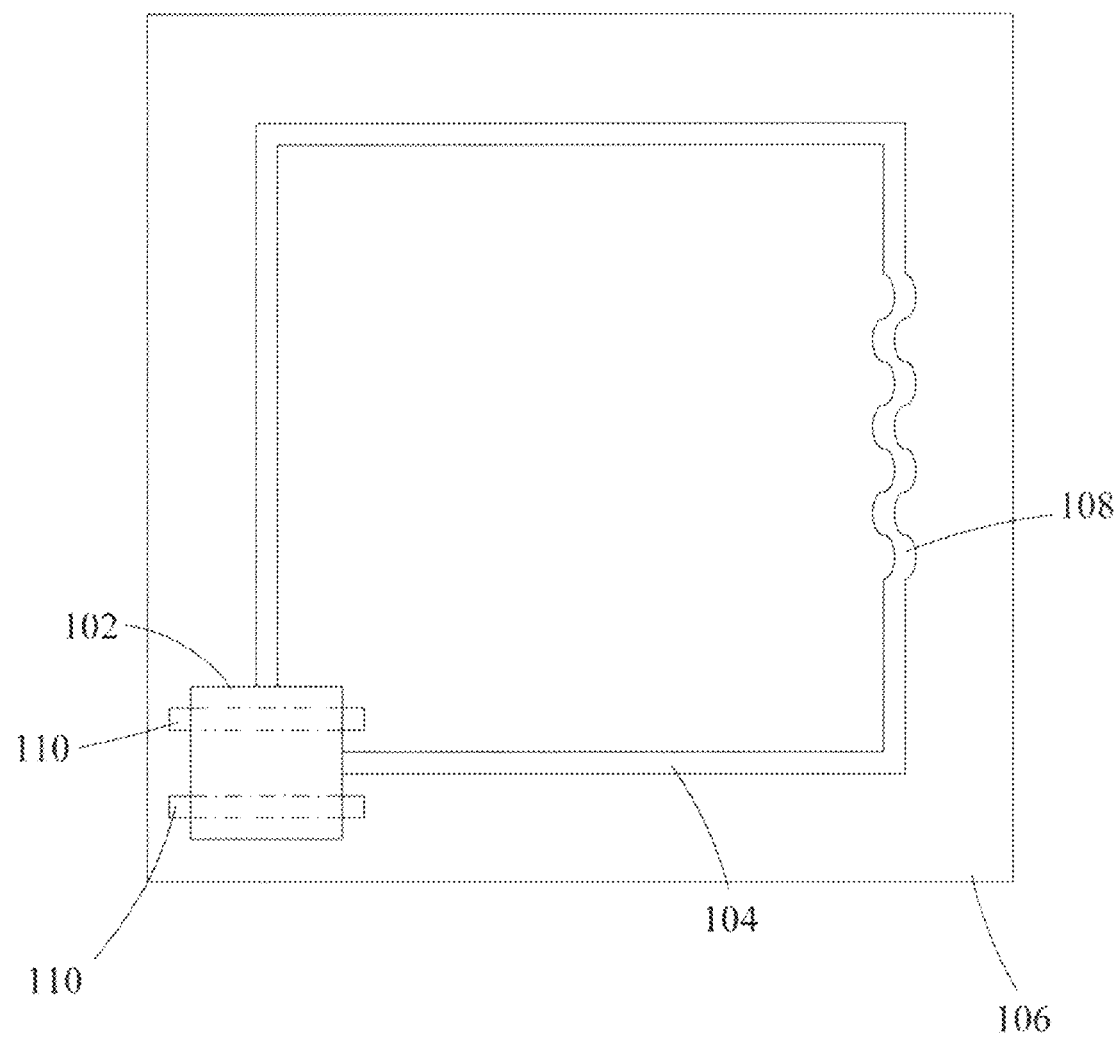
FIG. 11 is a view of the RFID device of the present invention.

As shown by FIG. 10, the nonactive tag receiver/transmitter system of the present invention does not operate in the typical RFID frequency range or by the same interrogation scheme. For nonactive tags the system uses a broad band 2.0 to 20.0 mSec pulsed energy design rather than cw (continuous wave), and is designed to operate only at shorter distances between nonactive and interrogator. The broadband 17 mSec pulse of low frequency (30 KHz-100 MHz) electromagnetic energy emitted from the transmitter interacts with the nonactive tag placed at distances from 0.5 to 100 m from the transmitter. The nonactive tags then oscillate at their unique frequencies for a period of time after the pulse stops determined by the Q of the nonactive tag circuit. These continued oscillations of the nonactive tag circuit elements are received by the interrogator and the precise frequency is converted into data information. For the completely organic implementation, the components of the preferred RFID device, including substrate, conductive trace, capacitor, and inductor are all constructed from organic, carbon-based materials, they are completely combustible at temperatures of 1000 degrees Celsius and less. This has been confirmed via thermogravimetric (TGA) analysis.

Figure 9:
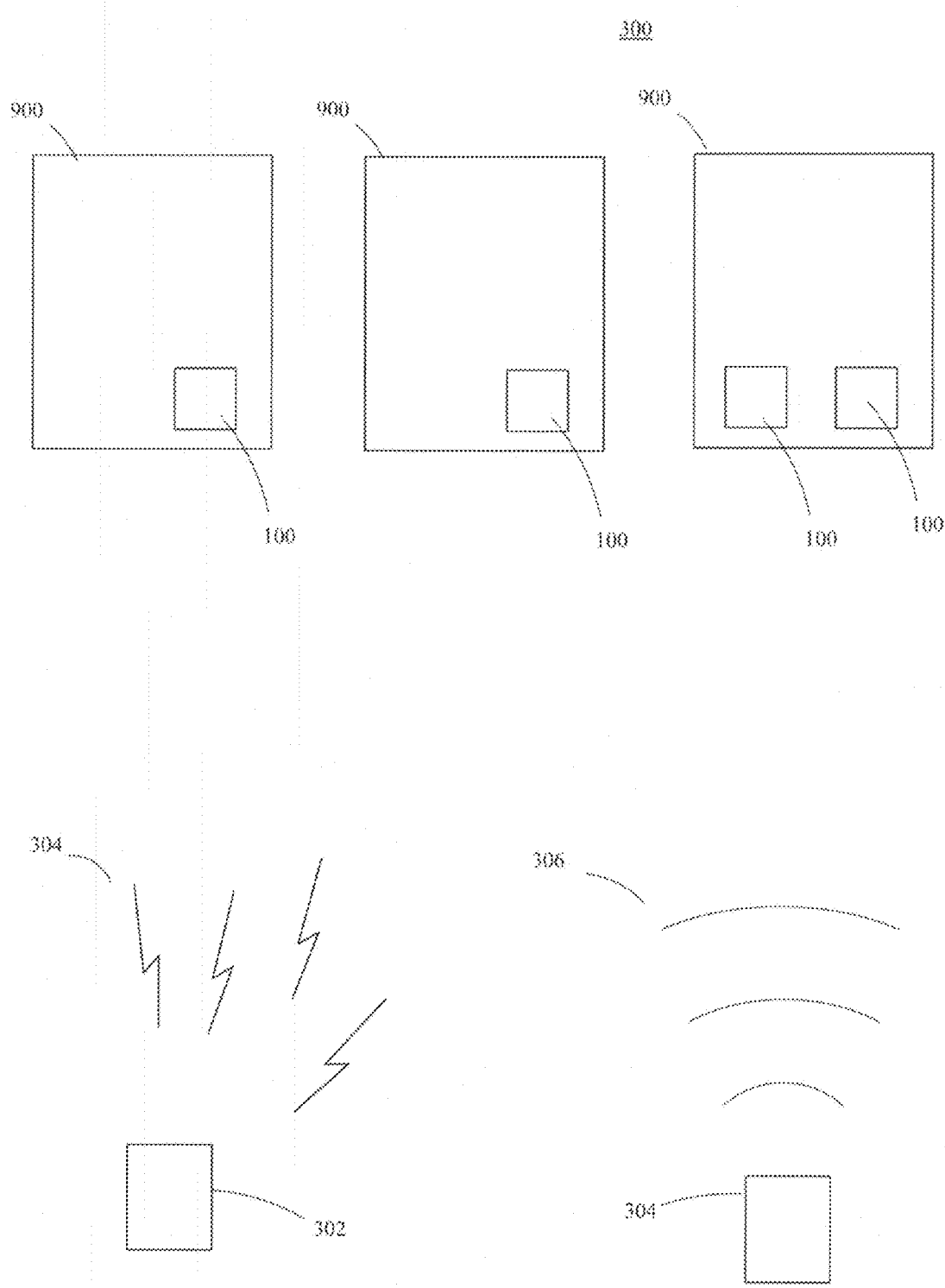
FIG. 9 is a view of the system of the present invention.

Turning to FIG. 9, the measurement system 300 of the present invention includes the RFID device placed proximate to an item 900. The electric components of the interrogator and receiver system uses an ultra high stability phase locked loop to measure the changes in nonactive tag frequency to greater than 1.0 ppm from the nonactive tag. The unit has a microprocessor and section that include the interrogator or transmitter, receiver, and Bluetooth or Wi-Fi networking that can be easily integrated for instantaneous data exchange to local or global networks.

An electromagnetic energy pulse will be emitted from the transmitter with the printed sensing element placed at carious pre-determined distances from the transmitter. The resonance frequency will be received by the receiver placed at various pre-determined distances from the sensing element. The step will determine the operation distance of the sensor system. Thermal cycling (−40 degrees C. to 65 degrees C.) of the sensing element will be conducted to further evaluate the sensing performance and the effect of thermal cycling on performance. As the components of the preferred RFID device, including substrate, conductive trace, capacitor, and inductor are all constructed from organic, carbon-based materials, they are completely combustible at temperatures of 1000 degrees C. and less.

Turning now to FIGS. 8 and 9, the measurement process 200 and measurement system 300 of the present invention is depicted. The RFID device 100 is associated 202 with an item 900. Suitable RFID devices for use in the process 200 and system 300 may include any version of the RFID device of the present invention described herein. The RFID device preferably used with the process 200 and system 300 preferably includes the inductor, the conductive antenna complex, a brace, and a capacitor. The brace is adapted to flex 242 in concert with exposure to a predetermined stimulus to actuate either the inductor or the capacitor. The braced component, either the inductor or capacitor, in its native, unexposed form, (i.e., has not been substantially exposed to an environment for measurement) retains the tight frequency tolerances to which it has been manufactured. The RFID device is manufactured to accept a signal at a predetermined base frequency.

The present invention may include a predetermined base frequency. Although the present invention describes frequency as the transmission parameter of the present invention, any signal characteristic may be measured if it is altered by the environmental stimulus. The predetermined base frequency is a base frequency that is known and at which the RFID device is adapted to respond. Because the base frequency is known, signal frequency response deviations from the base frequency value may be measured and information may be determined therefrom. The RFID device may also be manufactured to respond with a signal at an arbitrary value and then that arbitrary signal may be uncovered subsequently to become a known frequency. Determination of, and then retention of such frequency, is a "predetermined" base frequency according to the present invention.

The predetermined base frequency is preferably associated with an RFID device having a substantially high Q-value. The high Q-value ensures a narrow range of acceptance of interrogation frequencies and transmission of response signals by the RFID device. The RFID device 100 is associated with any item 900 in which a measurement of the effects of environmental stimulus is desired. The preferred item 900 of the present invention includes items that are stored for prolonged periods of time, and that have characteristics that are substantially alterable during storage based on the effects of an environmental stimulus. An exemplary item 900 includes artillery ammunition. Artillery ammunition may be stored for prolonged periods of time prior to use, and water vapor in the atmosphere in the storage location may affect the characteristics of the artillery ammunition. The RFID device 100 may be affixed either to a specific unit of artillery ammunition as the item of the present invention—or the item of the present invention may include a container that holds one or more artillery ammunition units. An association for the purposes of the present invention includes a connection that permits the environmental effects to act to a generally equal degree on both the item and the RFID device. The preferred means of associating 202 includes physically affixing the RFID device 100 to the item 900. The brace of the RFID device deforms 242 in response to exposure to the environment stimulus.

An interrogation signal 306 is radiated 204 from an interrogation device 304 in range for the RFID device 100 to receive the interrogation signal. The preferred means of radiating 204 an interrogation signal is to broadcast a range of signal frequencies correlated to the predetermined base frequency of an RFID device expected to be found in the range vicinity of the interrogation signal. For example, if the predetermined base frequency of an RFID device expected to be found within range of the interrogation device is 25 MHz, then the interrogation device may transmit an array of signals centered around 25 MHz, such as 24-26 MHz at 0.001 MHz increments. It is preferred that the interrogation signal is informed by the predetermined base frequency; in other words, the interrogation signal is selected by knowledge of likely characteristics of the predetermined base frequency. It is a characteristic of hi-Q RFID devices that the nature of the high-quality construction requires more precise signals for reception by the RFID device; however, the RFID device similarly transmits crisper signals with a tighter range of frequency variance. It is preferred that the interrogation signal include multiple frequencies broadcast substantially simultaneously or sequentially, the multiple frequencies need not include the predetermined base frequency. The range of frequencies may be entirely above the predetermined base frequency or entirely below the predetermined base frequency.

A response signal 304 from at least one RFID device 100 that accepted an interrogation signal 306 is received 206. The response signal 304 may be received on the interrogation device 304 that broadcast the interrogation signal 306 or a second device. The response signal 304 need not include any information. It is, however, preferred that the response signal include at least an identification, e.g. a serial number, of the RFID device from which the signal originated or an indication of the predetermined base signal from which of the RFID device from which the signal originated. The primary information determined from the response signal is determined not necessarily in information embedded within the RFID device transmission, but rather the frequency of the transmission.

The response signal is compared 208 to the predetermined base frequency of the RFID. The predetermined base signal may be determined via multiple methods. In a first exemplary method, the RFID device as associated with the item may have a visual display that indicates the predetermined base frequency. An example of a visual display includes a hangtag or cover that specifically references the predetermined base signal. In a second exemplary method, the RFID device may digitally transmit as information the predetermined base signal. In a third method, the RFID device may transmit an identification, e.g. a serial number, that is used to reference the predetermined base frequency. Any other known means of determining a base frequency of an RFID device or revealing information may be utilized to reveal the predetermined base frequency of one or more RFID devices.

A preferred means of indicating the predetermined base frequency utilizes a table of RFID identifications and their respective predetermined base frequencies. This table may reside in a correlation database 212. In comparing 208 the base signal frequency to the response signal of one or more RFID devices, information concerning the state of the RFID device, and in turn the associated item, is revealed in the deviations of characteristics of the response signal from known characteristics of the predetermined base signal frequency. The resulting deviation informs a measurement 210 based on the deviation. There are two preferred means of arriving at a measurement 210, contemporaneous calculations and use of correlations from the correlations database. The contemporaneous calculation method includes the use of machine-aided calculations to utilize an equation that includes the deviation as a variable to determine the effects of environmental stimulus. The correlation method may include a table, or other data comparison means, that includes a series of deviation values correlated to an environmental effects value for each deviation value in the deviation value series. Such a table may include other variable that may be measured, for example, by the transmission device. The resulting measurement of the environmental stimulus effect may be used for any purpose for which knowledge of the environmental stimulus effect is relevant. For example, in artillery ammunition, a measurement of vapor absorption may be utilized as a variable in rapid trajectory calculations.

Figure 17:
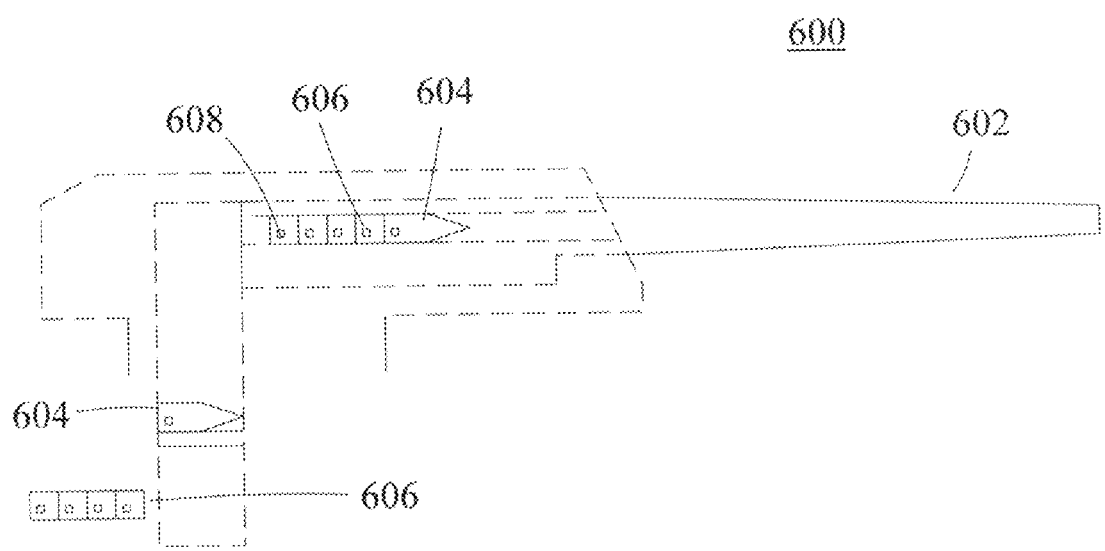
FIG. 17 is a view of the combustion system of the present invention.
Figure 18:
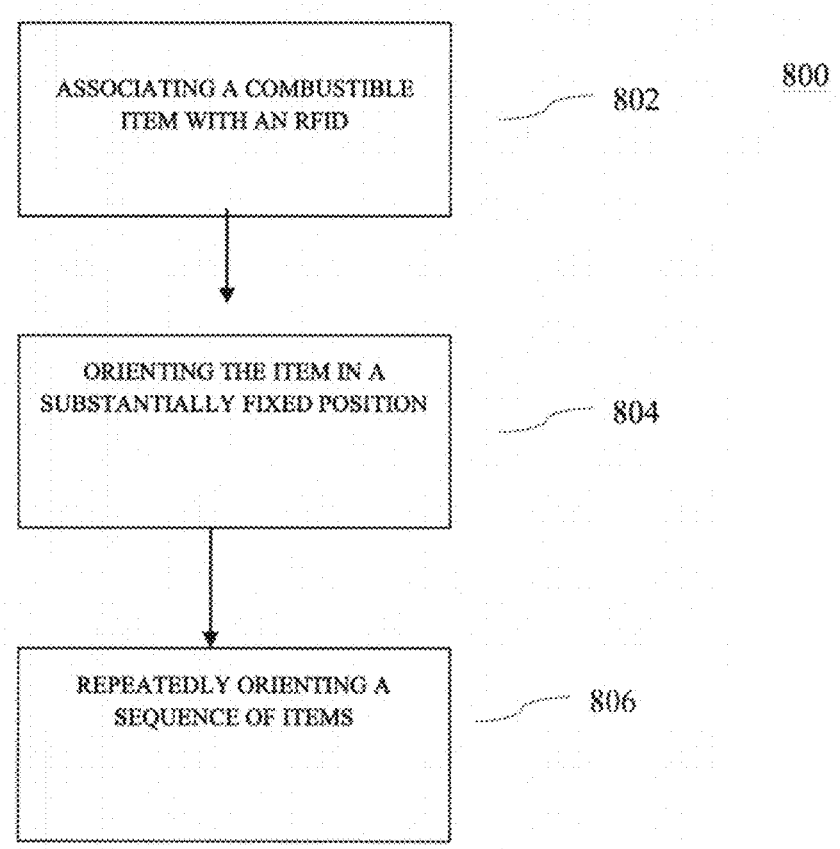
FIG. 18 is a view of the clean measurement process of the present invention.

As FIGS. 17-18 show, the organic construction of an RFID device as disclosed herein lends itself to other advantages, including in clean measurement systems 600. An RFID composed entirely of organic materials combusts. Combustion is a preferred means of removing an RFID because the byproducts of the combustion consist of gases without leaving material residue. The clean combustion and measurement system 600 includes one or more items beneficial to measure. An exemplary 600 is an artillery weapon 602. The weapon 602 includes as items a projectile 604 and powder charges 606—although many weapon systems will combine the charge and projectile into a single unit. The items are transitory in that they only spend a short portion of their useful life in an active state, for example here, in a gun barrel. In one embodiment of the clean measurement system and process 800, an RFID device 608 is associated 802 with the projectiles and powder such that the RFID device measures environmental stimulus that has acted upon the items. Here, the measurement of environmental stimulus, e.g. moisture to which the item has been exposed, is read shortly prior to firing the projectile and becomes a variable in the firing calculation of the weapon.

The RFID device is entirely organic. Because the energy given off by firing the projectile may be readily ascertained, materials that substantially combust under that energy level may be used in construct the RFID device. By substantially combust, it is meant that the RFID combusts at a level that the residue becomes statistically insignificant in calculations related to the use of the item at the time of measurement. The combustion energy may derive from the item being measured, in the example of the powder charge as the measured item, or the combustion energy may derive from an external energizer, in the example of the projectile as the measured item. The present invention is particularly useful in situations in which an item is replaced 806 by a second item, and so on sequentially, that shares its fixed orientation 804. In the example of artillery, because each projectile occupies substantially the same position as the projectile before it, it is affected by the residue of the prior projectile and its ancillary components. Residue in artillery barrels causes variations in projectile trajectories. The present invention substantially nullifies deviation that might result from measuring weapon system stimulus exposure via RFID. Flame temperature is very close to the same for all smokeless powders and runs about 3300 degrees F. Ball type powders tend to be from 3200 to 3300 degrees F. and extruded powders tend to run 3300 to 3400 degrees F. but there is wide variation.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. An RFID device comprising:
   a substrate composed of a first material;
   an inductor having an inductance and multiple conductive, repeating subfeatures;
   a conductive trace, integrated with said substrate, having an elastic connection with said inductor;
   a capacitor, supported by said substrate, with a voltage potential;
   a deformable brace, intercalated within said inductor between at least one pair of said repeating subfeatures, constructed from a second material structurally, selectively deformable in response to a predetermined external stimulus such that upon exposure to said stimulus said inductor is dimensionally altered by said brace, disproportionately to a response by said first material to said external stimulus, to substantially alter said inductance; and
   an antennae complex, in electrical communication with said inductor supported by said substrate and isolated from said second material, initially adapted to accept a predetermined, base frequency and transmit a response signal, measurably distinct from said base frequency when affected by said inductance as altered by said brace,
   wherein said elastic connection is adapted to maintain inductor circuit connectivity notwithstanding said substantially disproportionate dimensional alterations of said second material relative to said first material.

2. The RFID device of claim 1 wherein said second material includes a time decay material adapted to decay at a decay rate substantially disproportionate to a decay rate of said first material.

3. The RFID device of claim 1 wherein said second material includes a temperature-sensitive material having a coefficient of expansion substantially disproportionate to a coefficient of expansion of said first material.

4. The RFID device of claim 1 wherein said second material includes a hyrdo-sensitive material adapted to dimensionally alter said brace upon absorption of water molecules to a degree substantially disproportionate to absorption of water molecules of said first material.

5. The RFID device of claim 1 wherein said brace includes a unidirectional brace.

6. The RFID device of claim 1 wherein said capacitor is isolated from said second material.

7. An RFID device comprising:
   a device substrate composed of a first material;
   an inductor, supported by said substrate, having an inductance;
   a plate capacitor, supported by said substrate, with a voltage potential, wherein said capacitor includes at least a first electrode; at least a second electrode; and discrete primary insulator, positioned between said first electrode and said second electrode such that said primary insulator lacks physical connection with any ancillary insulator separating any third electrode from said first electrode and said second electrode, composed of a dielectric material;
   a conductive trace, integrated with said substrate, having an elastic connection with said capacitor;
   a deformable brace, distinct from said insulator and supported by said substrate and positioned proximate to said capacitor, constructed from a second material structurally, selectively deformable in response to a predetermined external stimulus such that upon exposure to said stimulus said capacitor is dimensionally altered by said brace, disproportionately relative to both a response by said first material to said external stimulus and said insulator to said external stimulus, to substantially alter said voltage potential; and
   an antennae complex, in electrical communication with said inductor supported by said substrate and isolated from said second material, initially adapted to accept a predetermined, base frequency and transmit a response signal, measurably distinct from said base frequency when affected by said voltage potential as altered by said brace,
   wherein said elastic connection is adapted to maintain capacitor circuit connectivity notwithstanding said substantially disproportionate dimensional alterations of said second material relative both to said first material and said insulator.

8. The RFID device of claim 7 wherein said second material includes a time decay material adapted to decay at a decay rate substantially disproportionate to a decay rate of said first material.

9. The RFID device of claim 7 wherein said second material includes a temperature-sensitive material having a coefficient of expansion substantially disproportionate to a coefficient of expansion of said first material.

10. The RFID device of claim 7 wherein said second material includes a hyrdo-sensitive material adapted to dimensionally alter said brace upon absorption of water molecules to a degree substantially disproportionate to absorption of water molecules of said first material.

11. The RFID device of claim 7 wherein said brace includes a unidirectional brace.

12. The RFID device of claim 11 wherein said capacitor is isolated from said second material.

13. An RFID device comprising:
    a substrate composed of a first material;

an inductor having an inductance and an inductor length defined as the Euclidean distance between lead points of said inductor;

a conductive trace, integrated with said substrate, having an elastic connection with said inductor;

a capacitor, supported by said substrate, with a voltage potential;

a deformable brace, in which said inductor is at least partially embedded to subsume at least 20% of said inductor length, constructed from a second material structurally, selectively deformable in response to a predetermined external stimulus such that upon exposure to said stimulus said inductor is dimensionally altered by said brace, disproportionately to a response by said first material to said external stimulus, to substantially alter said inductance; and an antennae complex, in electrical communication with said inductor supported by said substrate and isolated from said second material, initially adapted to accept a predetermined, base frequency and transmit a response signal, measurably distinct from said base frequency when affected by said inductance as altered by said brace, wherein said elastic connection is adapted to maintain inductor circuit connectivity notwithstanding said substantially disproportionate dimensional alterations of said second material relative to said first material.

14. The RFID device of claim 13 wherein said inductor is at least partially embedded in said brace to subsume at least 20% of said inductor length.

15. The RFID device of claim 14 wherein said inductor is at least partially embedded in said brace to subsume at least 30% of said inductor length.

16. The RFID device of claim 15 wherein said inductor is at least partially embedded in said brace to subsume at least 40% of said inductor length.

17. The RFID device of claim 16 wherein said inductor is at least partially embedded in said brace to subsume at least 50% of said inductor length.

18. The RFID device of claim 17 wherein said inductor is at least partially embedded in said brace to subsume at least 75% of said inductor length.

19. The RFID device of claim 18 wherein said inductor is at least partially embedded in said brace to subsume at least 90% of said inductor length.

20. The RFID device of claim 19 wherein said inductor is at least partially embedded in said brace to subsume at least 100% of said inductor length.

* * * * *